US012755840B2

(12) United States Patent
Vincent Salomon et al.

(10) Patent No.: US 12,755,840 B2
(45) Date of Patent: Oct. 6, 2026

(54) PREDICTION OF BRCANESS/HOMOLOGOUS RECOMBINATION DEFICIENCY OF BREAST TUMORS ON DIGITALIZED SLIDES

(71) Applicants: INSTITUT CURIE, Paris (FR); INSERM (Institut National de la Santé et de la Recherche Médicale), Paris (FR); ECOLE NATIONALE SUPERIEURE DES MINES DE PARIS, Paris (FR)

(72) Inventors: Anne Vincent Salomon, Paris (FR); Thomas Walter, Paris (FR); Etienne Decencière, Avon (FR); Tristan Lazard, Paris (FR); Guillaume Bataillon, Toulouse (FR)

(73) Assignees: Institut Curie, Paris (FR); Institut National de la Sante et de la Recherche Medicale (INSERM), Paris (FR); Ecole Nationale Superieure des Mines de Paris, Paris (FR)

( * ) Notice: Subject to any disclaimer, the term of this patent is extended or adjusted under 35 U.S.C. 154(b) by 374 days.

(21) Appl. No.: 18/292,903

(22) PCT Filed: Jul. 27, 2022

(86) PCT No.: PCT/EP2022/071130
§ 371 (c)(1),
(2) Date: Jan. 27, 2024

(87) PCT Pub. No.: WO2023/006843
PCT Pub. Date: Feb. 2, 2023

(65) Prior Publication Data

US 2024/0371520 A1 Nov. 7, 2024

(30) Foreign Application Priority Data

Jul. 28, 2021 (EP) .................................... 21306055
Jul. 28, 2021 (EP) .................................... 21306056

(51) Int. Cl.
*G06K 9/00* (2022.01)
*G06V 10/42* (2022.01)
(Continued)

(52) U.S. Cl.
CPC ............. *G16H 50/20* (2018.01); *G06V 10/42* (2022.01); *G06V 10/774* (2022.01); *G06V 10/82* (2022.01);
(Continued)

(58) Field of Classification Search
USPC ....... 382/100, 103, 128, 133, 156, 168, 173, 382/181, 254, 305, 312; 506/9
See application file for complete search history.

(56) References Cited

U.S. PATENT DOCUMENTS

2016/0160293 A1* 6/2016 Tutt ....................... A61K 45/06
506/9
2017/0260588 A1* 9/2017 Manie .................. A61K 33/243
(Continued)

OTHER PUBLICATIONS

Valieris et al., "Deep Learning Predicts Underlying Features on Pathology Images with Therapeutic Relevance for Breast and Gastric Cancer," Cancers, 12: 3687 (2020).
(Continued)

*Primary Examiner* — Seyed H Azarian
(74) *Attorney, Agent, or Firm* — Morgan, Lewis & Bockius LLP

(57) ABSTRACT

The present application relates to a computer-implemented method for identifying at least one class of at least one biological image, notably to predict the genomic signature from biological image(s), in particular to predict Homolo-
(Continued)

(start)

(end)

gous Recombination DNA-repair deficiency (HRD) from biological images of tissues. The present application further proposes a computer-implemented method for visualizing clusters of sub-images or tiles of at least one biological image, in particular to predict the phenotypic feature or combination of phenotypic features (or phenotypic patterns) associated with the genomic signature.

23 Claims, 6 Drawing Sheets

(51) Int. Cl.

| | |
|---|---|
| ***G06V 10/774*** | (2022.01) |
| ***G06V 10/82*** | (2022.01) |
| ***G06V 20/69*** | (2022.01) |
| ***G06V 20/70*** | (2022.01) |
| ***G16H 50/20*** | (2018.01) |

(52) U.S. Cl.
CPC .......... *G06V 20/695* (2022.01); *G06V 20/698* (2022.01); *G06V 20/70* (2022.01); *G06V 2201/03* (2022.01)

(56) References Cited

U.S. PATENT DOCUMENTS

2020/0258223 A1* 8/2020 Yip .......................... G06T 1/20
2020/0388029 A1* 12/2020 Saltz .................... G06V 10/267
2021/0319906 A1* 10/2021 Hafez .................... G16H 20/00
2024/0144477 A1* 5/2024 Kanan .................. G06V 10/462
2025/0129426 A1* 4/2025 Yen ........................ G16B 30/20

OTHER PUBLICATIONS

Schirris et al., "DeepSMILE: Self-supervised heterogeneity-aware multiple instance learning for DNA damage response defect classification directly from H&E whole-slide images," ARXIV.org (2021).
Taylor-Weiner et al., "Abstract PD6-04: Deep-learning based prediction of homologous recombination deficiency (hrd) status from histological features in breast cancer; a research study," Cancer Research, 81 (Supplement 4): 1-04 (2021).
Written Opinion issued in International Patent Application No. PCT/EP2022/071130 dated Jan. 2, 2023.
Tomita et al., "Finding a Needle in the Haystack: Attention-Based Classification of High Resolution Microscopy Images," ARXIV.org, Cornell University Library (2018).

* cited by examiner

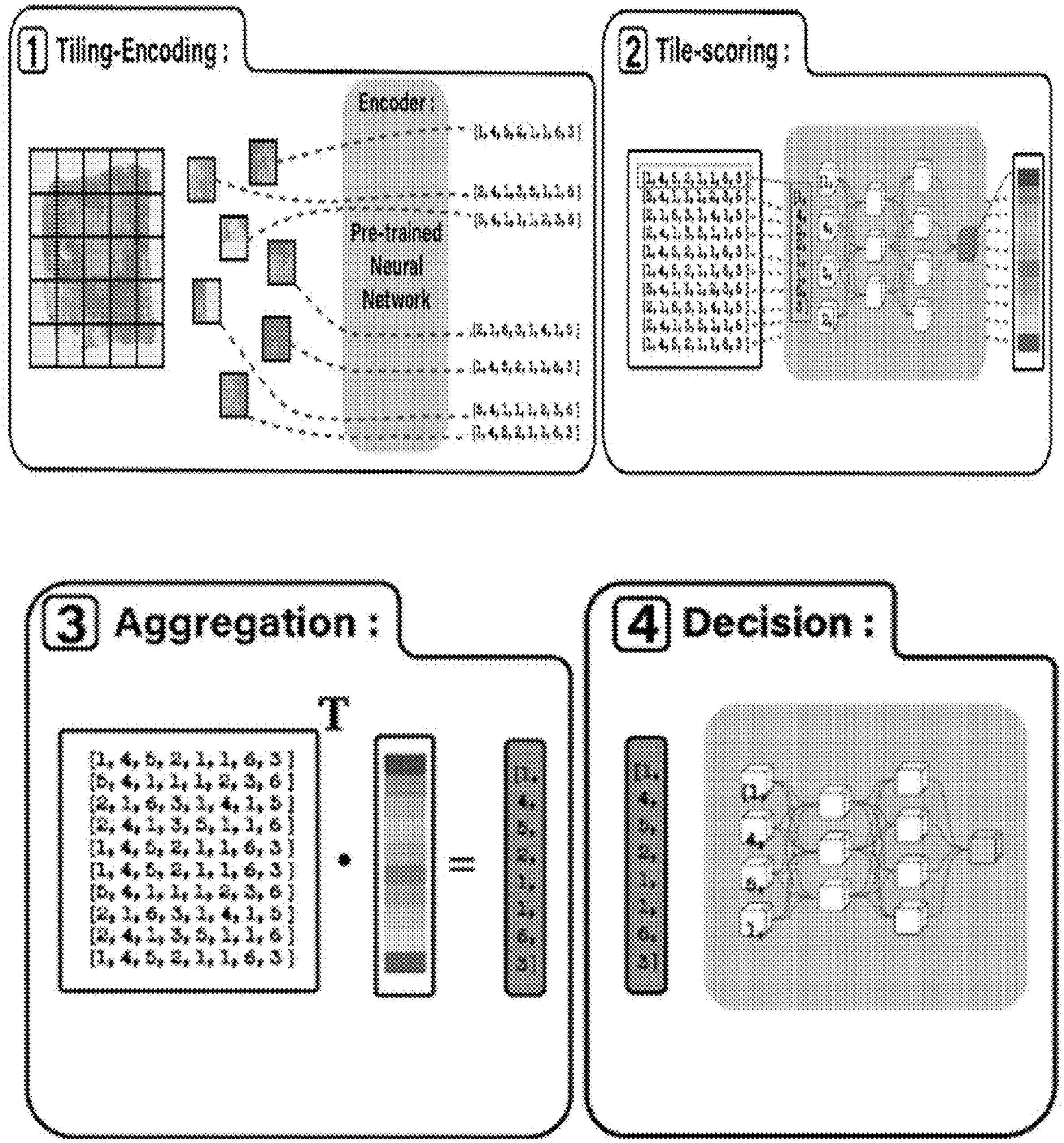
Figure 1 (start)

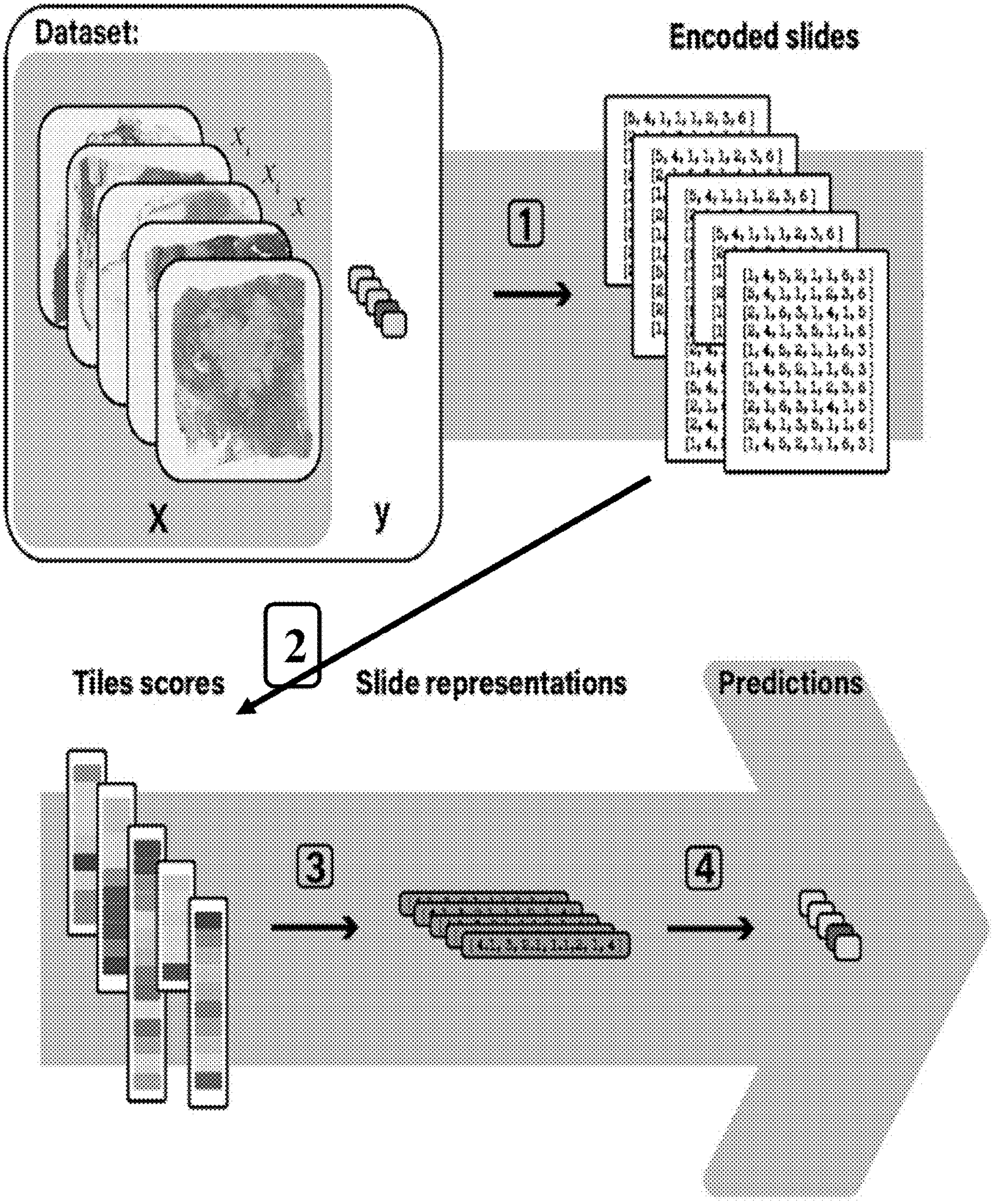
Figure 1 (end)

d

| | AUC | | $B_{Acc}$ | |
|---|---|---|---|---|
| | mean | std | mean | std |
| TCGA *raw* | **0.71** | 0.1 | **0.59** | 0.08 |
| TCGA $c_3$ | **0.63** | 0.08 | **0.54** | 0.02 |
| Curie *raw* | **0.88** | 0.03 | **0.81** | 0.02 |
| Curie $c_1 + c_2$ | **0.86** | 0.03 | **0.78** | 0.04 |
| Curie *luminals* | **0.83** | 0.07 | **0.72** | 0.06 |

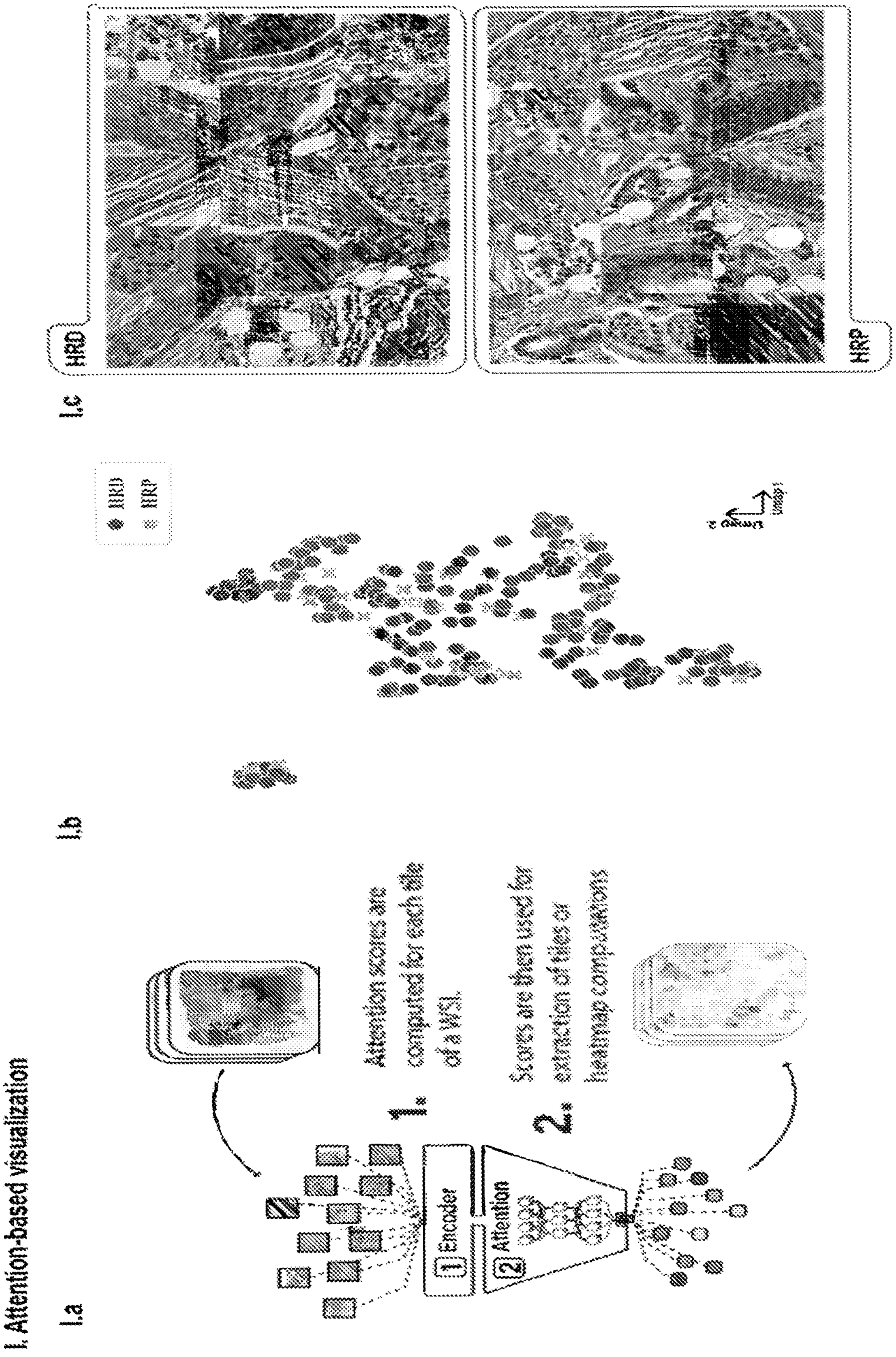
Figure 3 (start)

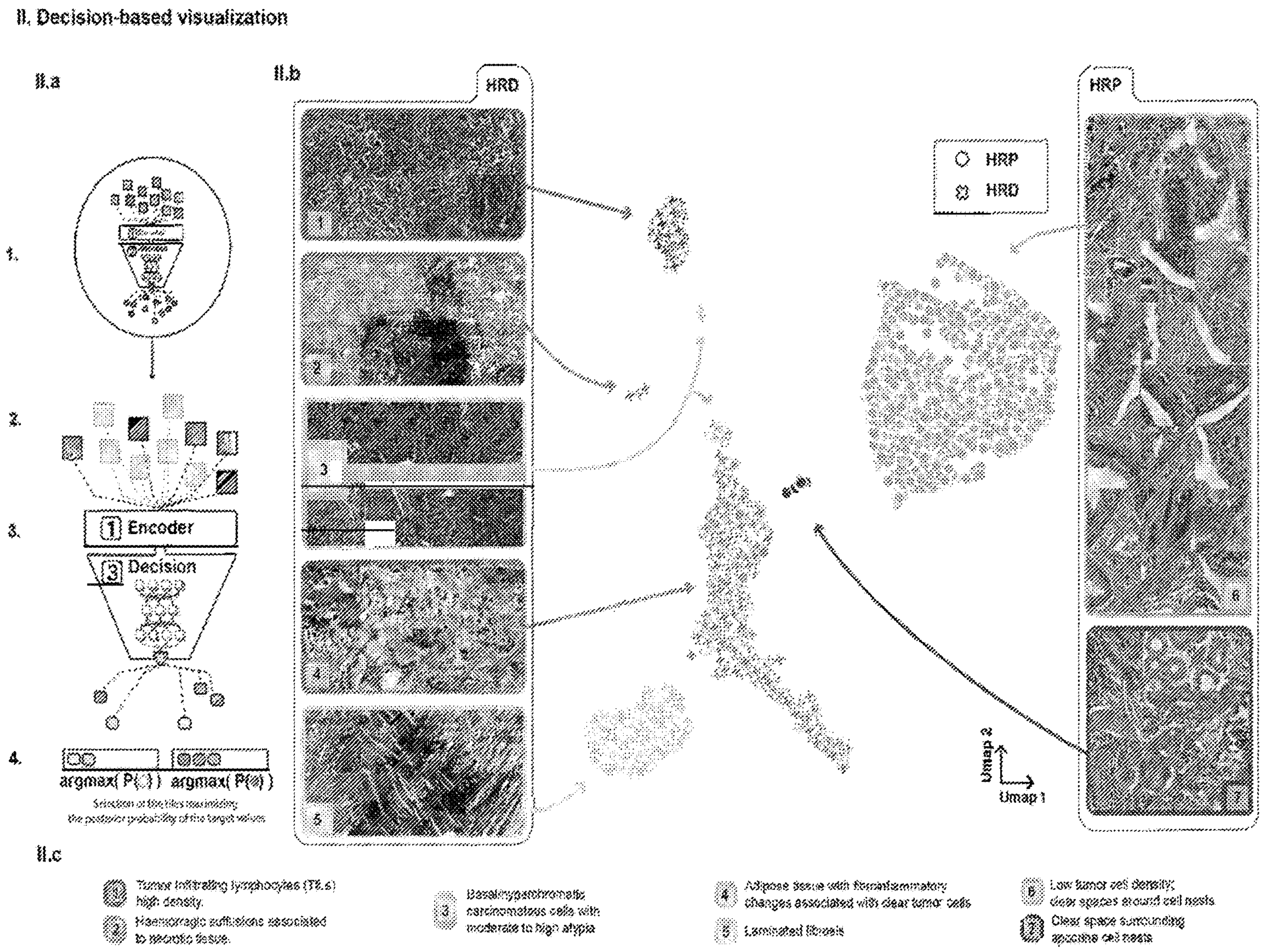
Figure 3 (end)

PREDICTION OF BRCANESS/HOMOLOGOUS RECOMBINATION DEFICIENCY OF BREAST TUMORS ON DIGITALIZED SLIDES

FIELD OF THE INVENTION

The present application relates to a computer-implemented method for identifying at least one class of at least one biological image, notably to predict the genomic signature from biological image(s), in particular to predict Homologous Recombination DNA-repair deficiency (HRD) from biological images of tissues. The present application further proposes a computer-implemented method for visualizing clusters of sub-images or tiles of at least one biological image, in particular to predict the phenotypic feature or combination of phenotypic features (or phenotypic patterns) associated with the genomic signature.

BACKGROUND OF THE INVENTION

Homologous Recombination DNA-repair deficiency (HRD) is a well-recognized marker of platinum-salt and PARP inhibitor chemotherapies in ovarian cancer and is under evaluation in clinical trials in breast cancers (BC). Causing high genomic instability, HRD is currently determined by BRCA1/2 sequencing or by genomic signatures, but its morphological manifestation is not well understood. Deep Learning is powerful machine learning technique that has been recently shown to be capable of predicting genomic signatures from stained tissue slides. Here, we train a deep-learning model to predict the HRD in a controlled cohort of luminal BC (AUC: 0.83). We present and evaluate a strategy to control for imaging biases in retrospective cohorts and we develop a new visualization technique that allows automatically extracting the morphological features related to HRD. The extracted morphological patterns have been analysed in detail leading to improve the understanding of the phenotypic impact of HRD.

The importance of correcting biases when predicting Homologous Recombination Deficiency (HRD) in breast cancers from Hematoxylin Eosin slides using deep learning is herein demonstrated. the novel interpretation algorithm leads to results illustrative of disease-relevant genotype-phenotype relationships, thus identifying morphological patterns related to HRD and shedding light on its phenotypic consequences.

DESCRIPTION OF THE INVENTION

The advent of Deep Learning has revolutionized biomedical image analysis and in particular digital pathology. Traditionally, the majority of methods developed in this field were dedicated to computer-aided diagnosis, where the objective is to partially automatize human interpretation of slides, in order to help pathologists in their diagnosis task, e.g. the detection of mitoses 1, or the identification of metastatic axillary lymph nodes 2,3. Beyond the automatization of manual inspection, Deep Learning has also been successfully applied to predict patient variables, such as outcome 4, and to predict molecular features, such as gene mutations 5,6, expression levels 7 or genetic signatures 5,8. Despite these results of unprecedented quality, one of the major drawbacks of Deep Learning algorithms is their black-box character: because the features are automatically extracted, it is difficult to know how a decision was made.

This has two major consequences: first, it is difficult to identify potential confounders, i.e. variables that correlate with the output due to the composition of the data set and that are predicted instead of the intended output variable. Second, even in the absence of statistical artifacts, understanding how the decision was generated in the first place can point to interesting mechanistic hypotheses and to patterns in the image that have so far been overlooked. One way to overcome the latter problem is to use hand-crafted biologically meaningful features 8. This however requires an extraordinary effort in terms of annotation. Here, we take a conceptually different approach. Instead of working in a pan-cancer setting on a large number of signatures, we concentrate on one single medically highly relevant signature in one cancer type on a controlled data set, where we can correct for potential biases. In order to understand how the Deep Learning decision is generated and which morphological patterns are related to the output variable, we propose a novel visualization and interpretation technique that paves the way to "machine teaching", i.e. a data driven approach to identify phenotypic patterns related to genomic signatures, thus pointing to new mechanistic hypotheses. In order to demonstrate the power of this strategy, we focus on predicting Homologous Recombination Deficiency (HRD) in Breast Cancer (BC). Worldwide, 2.1 million women are newly diagnosed per year with BC which is a leading cause of cancer-related death. Improvement of metastatic breast cancer treatment is therefore of highest priority. BC is a heterogeneous disease with four major molecular classes (luminal A, B, HER2 enriched, and triple-negative breast cancer [TNBC]) benefiting from different therapeutic approaches. If early BC patients have an overall survival of 70 to 80%, metastatic disease is incurable with a short duration of survival 9. Homologous Recombination (HR) is a major and high-fidelity repair pathway of DNA double-strand breaks. Its deficiency, HRD, results in high genomic instability 10 and occurs through diverse mechanisms, including germline or acquired mutations in DNA repair genes, most frequently BRCA1, BRCA2 or PALB2, or through epigenetic alterations of BRCA1 or RAD51C. Importantly, HRD leads to a high sensitivity to polyADP-ribose polymerase inhibitors (PARPi) in vitro 11,12. PARPi have been shown to improve metastatic breast cancer progression free survival 13. Several methods have been developed to detect HRD, including genomic instability profiling, mutational signatures, or integrating structural and mutational signatures 14-18. However, HRD is currently diagnosed in clinical practice by DNA repair genes sequencing and genomic instability patterns (genomic scar) such as the LST signature 14 or the HRD MyChoice® CDx test (Myriad Genetics). BRCA1 and BRCA2 mutations are known predictive markers for response to PARPi 10 and platinum salt 19 and the somatic HRD has been more recently recognized as a predictive marker for PARPi in ovarian 10 and breast cancer 20. But neither a specific routinely assessed phenotype nor a morphological pattern indicates the presence of HRD. The majority of hereditary BRCA1 cancers are TNBC and up to 60-69% of sporadic TNBC harbor a genomic profile of HRD (Alexandrov et al. 2013; Popova et al. 2012; Chopra et al. 2020). However, the majority of hereditary BRCA2 cancers are luminal (Lakhani et al. 2002) and HRD also exists in sporadic luminal B (Manié et al. 2016; Chopra et al. 2020) or in HER2 tumors (Ferrari et al. 2016; Turner 2017). Of note, germline or sporadic alterations of BRCA harbor indistinguishable genomic alterations in triple-negative or in luminal tumors 21,22. In that context, a reliable and accurate test is mandatory to select patients for PARPi and platinum salt treatments. Whereas the screening for germline or somatic BRCA1 and BRCA2 mutations is feasible for all TNBC (18% of all BC cases), it represents a real challenge in clinical practice if extended to all luminal B tumors (35% of all BC). This strategy moreover does not identify the whole diversity of genetic causes of HRD. In this study, we present an image-based approach to predict HR status from Whole Slide Images (WSI) stained with Hematoxylin Eosin (HE) using deep learning, from a large retrospective series of luminal and triple-negative breast carcinomas with a genomically defined HR status, from a single cancer center. In particular, we show that careful correction for potential biases is essential for such studies and demonstrate the relevance of a correction strategy. Finally, we develop a novel interpretation algorithm that allows the visualization of decisive patterns and leads to new hypotheses on disease-relevant genotype-phenotype relationships.

The principle of the invention is notably illustrated in the FIGS. 1 and 3 (see also the associated material and methods section) of the enclosed results. The present invention is illustrated with WSI obtained from stained tissue slides (notably Hematoxylin Eosin slides) from breast cancer, the principles of the present application can be extended to any cancer and/or biological image and typically implemented according to the embodiments as described below.

A cancer is a disease involving abnormal cell growth with the potential to invade or spread to other parts of the body. According to the invention, the cancer which affects or affected a patient may be selected from the list consisting of bladder cancer, bone cancer, brain cancer, breast cancer, cervical cancer, colon cancer, esophageal cancer, gastric cancer, head & neck cancers, hodgkin's lymphoma leukemia, liver cancer, lung cancer, melanoma, mesothelioma, multiple myeloma myelodysplastic syndrome, non-hodgkin's lymphoma, ovarian cancer, pancreatic cancer, prostate cancer, rectal cancer, renal cancer, sarcoma, skin cancer, testicular cancer, thyroid cancer or uterine cancer. In a particular embodiment, the cancer which affect or affected a patient is a breast cancer, including breast cancer corresponding to ductal carcinoma, lobular carcinoma, invasive breast cancer, inflammatory breast cancer, metastatic breast cancer, hormone receptor positive breast cancer, hormone receptor negative cancer, HER2 positive breast cancer, HER2 negative breast cancer, triple-negative breast cancer. In a more particular embodiment of the invention, the cancer which affects or affected a patient is a triple-negative breast cancer. Triple-negative breast cancer (TNBC) is cancer that tests negative for estrogen receptors, progesterone receptors, and excess HER2 protein. Thus, triple-negative breast cancer does not respond to hormonal therapy medicines or medicines that target HER2 protein receptors.

A biological marker (or biomarker) is defined as a biochemical, molecular, or cellular alteration that is measurable in biological media such as tissues, cells, or fluids, and that indicates normal or abnormal process of a condition or disease. The term "biomarker" refers to molecule which can be measured accurately and reproducibly, thereby leading to the provision of a "signature" that is objectively measured and evaluated as an indicator of normal biological processes, or pathogenic processes, or pharmacologic responses. In the context of the present invention, a biomarker corresponds to biological molecule(s) expressed by and/or present within cells of a human being. Thus, in the present invention biological markers include genetic biomarkers (corresponding to the transcript products of genes) and epigenetic biomarker (corresponding to methylation of DNA for example). In the present invention, biomarkers include DNA, RNA and proteins. The measure of the expression of the biomarkers leads to the provision of a signature that can be associated with the detection of cancer cells.

A biological sample obtained from the patient can be any biological sample, such tissue, blood, urine, whole cell lysate. Methods of obtaining a biological sample are well known in the art and include obtaining samples from surgically excised tissue. Tissue, blood, urine and cellular samples can also be obtained without the need for invasive surgery, for example by puncturing the subject with a fine needle and withdrawing cellular material or by biopsy. In certain embodiments, samples taken from a patient can be treated or processed to obtain processed biological samples such as supernatant, whole cell lysate, or fractions or extract from cells obtained directly from the patient. In other embodiments, biological samples issued from a patient can also be used with no further treatment or processing. In a preferred embodiment, the biological sample obtained from the subject is a tissue, in particular a tissue from a tumor or a tumor extract, obtained by biopsy or by surgical excision. A biological sample issued from a subject may, for example, be a sample removed or collected or susceptible of being removed or collected from an internal organ or tissue or tumor of said subject, in particular from tumor, or a biological fluid from said subject such as the blood, serum, plasma or urine. A biological sample collected or removed from the subject may, for example, be a sample comprising cancer cells which have been or are susceptible of being removed or collected from a tissue, in particular a tumor, of said subject.

A primary cancer develops at the anatomical site where tumor progression began and proceeded to yield a cancerous mass. Most cancers develop at their primary site but then go on to metastasize: cancer cells from the primary cancer spread to other parts of the body and form new, or secondary, tumors, leading to a metastatic cancer. These secondary tumors are the same type of cancer as the primary cancer also called primary tumor. Most cancers continue to be called after their primary site, as in breast cancer or lung cancer for example, even after they have spread to other parts of the body.

A tumor is an abnormal mass of tissue that forms when cells grow and divide more than they should or do not die when they should. Tumors may be benign (not cancer) or malignant (cancer). Benign tumors may grow large but do not spread into, or invade, nearby tissues or other parts of the body. Malignant tumors can spread into, or invade, nearby tissues. They can also spread to other parts of the body through the blood and lymph systems.

Histopathology is a branch of pathology which deals with the study of disease in a tissue section. It may refer to the examination of a biopsy or a surgical specimen after the specimen has been processed and histological sections have been placed onto appropriate support medium.

A genomic signature or profile (or gene signature or gene expression signature or profile) is a single or combined group of genes in a cell with a uniquely characteristic pattern of gene expression that occurs as a result of an altered or unaltered biological process or pathogenic medical condition.

Homologous recombination (HR) is a type of genetic recombination in which genetic information is exchanged between two similar or identical molecules of double-stranded or single-stranded nucleic acids (usually DNA as in cellular organisms but may be also RNA in viruses). It is widely used by cells to accurately repair harmful breaks that occur on both strands of DNA, known as double-strand breaks (DSB), in a process called homologous recombinational repair (HRR).

Homologous recombination deficiency (HRD) is a phenotype that is characterized by the inability of a cell to effectively repair DNA double-strand breaks using the homologous recombination repair (HRR) pathway. Loss-of-function genes involved in this pathway can sensitize tumors to particular treatments which target the destruction of cancer cells, for example by working in concert with HRD through synthetic lethality.

Homologous recombination proficiency corresponds to a sample exhibiting a normal or near normal level of homologous recombination DNA repair activity.

Homologous recombination (HR) status of the cancer tissue corresponds to the classification of cancer into the group of homologous recombination deficient (HRD) or non-HR deficient (non HRD) (or HR proficient (HRP)).

A large-Scale State transition corresponds to a chromosomal breakage that generates 10 Mb or larger fragments. The quantification of these breaks can be used as a surrogate measure for genomic instability, which may be caused by mutation of DNA repair genes, including BRCA1 or BRCA2.

A molecular subtype or class of cancer is based in the genes the cancer cells express. These genes control how the cell behave. Different cancers of a single organ may behave and grow in different ways. Defining a cancer at the molecular, or smallest cell, allows to further classify cancers relatively to their pattern and behavior instead of their origin. As an example, breast cancer has four primary molecular subtypes, defined in large part by hormone receptors (HR) and other types of proteins involved (or not involved) in each cancer: a) Luminal A or HR+/HER2− (HR-positive/HER2-negative); b) Luminal B or HR+/HER2+ (HR-positive/HER2-positive); c) Triple-negative or HR−/HER2− (HR/HER2-negative); and d) HER2-positive. A fifth subtype, known as normal-like breast cancer, closely resembles luminal A.

A cancer's grade describes how abnormal the cancer cells and tissue look when compared to healthy cells. Cancer cells that look and organize most like healthy cells and tissue are low grade tumors. Some cancers have their own system for grading tumors. Many others use a standard 1-4 grading scale.

Grade 1: Tumor cells and tissue looks most like healthy cells and tissue. These are called well-differentiated tumors and are considered low grade.

Grade 2: The cells and tissue are somewhat abnormal and are called moderately differentiated. These are intermediate grade tumors.

Grade 3: Cancer cells and tissue look very abnormal. These cancers are considered poorly differentiated, since they no longer have an architectural structure or pattern. Grade 3 tumors are considered high grade.

Grade 4: These undifferentiated cancers have the most abnormal looking cells. These are the highest grade and typically grow and spread faster than lower grade tumors.

A cancer's stage describes how large the primary tumor is and how far the cancer has spread in the patient's body. There are several different staging systems. Many of these have been created for specific kinds of cancers. Others can be used to describe several types of cancer.

Stage 0 to stage IV: one common system that many people are aware of puts cancer on a scale of 0 to IV.

Stage 0 is for abnormal cells that haven't spread and are not considered cancer, though they could become cancerous in the future. This stage is also called "in-situ."

Stage I through Stage III are for cancers that haven't spread beyond the primary tumor site or have only spread to nearby tissue. The higher the stage number, the larger the tumor and the more it has spread.

Stage IV cancer has spread to distant areas of the body.

A sporadic cancer is a cancer that occurs in people who do not have a family history of that cancer or an inherited change in their DNA that would increase their risk for that cancer.

A germline cancer occurs when cancer is related to a mutation inherited from a parent. Germline mutations, also called hereditary mutations, are passed on from parents to offspring. Inherited germline mutations play an important role in cancer risk and susceptibility.

Major molecular subtypes of breast cancers are summarized in the table below (issued from Eliyatkin N. et al., J Breast Health. 2015 Apr. 1; 11 (2): 59-66. doi: 10.5152/tjbh.2015.1669).

| | Luminal A | Luminal B | HER2/neu | Basal like |
|---|---|---|---|---|
| Gene Expression pattern | Expression of luminal (low molecular weight) cytokeratins, high expression of hormone receptors and related genes | Expression of luminal (low molecular weight) cytokeratins, moderate-low expression of hormone receptors and related genes | High expression of HER2/neu, low expression of ER and related genes | High expression of basal epithelial genes and basal cytokeratins, low expression of ER and related genes, low expression of HER2/neu |
| Clinical and biologic properties | 50% of invasive breast cancer, ER/PR positive, HER2/neu negative | 20% of invasive breast cancer, ER/PR positive, HER2/neu expression variable, higher proliferation than Luminal A, higher histologic grade than Luminal A | 15% of invasive breast cancer, ER/PR negative, HER2/neu positive, high proliferation, diffuse TP53 mutation, high histologic grade and nodal positivity | ~15% of invasive breast cancer, most ER/PR/HER2/neu negative (triple negative), high proliferation, diffuse TP53 mutation, BRCA1 dysfunction (germline, sporadic) |

-continued

| | Luminal A | Luminal B | HER2/neu | Basal like |
|---|---|---|---|---|
| Histologic correlation | Tubular carcinoma, Cribriform carcinoma, Low grade invasive ductal carcinoma, NOS, Classic lobular carcinoma[b] | Invasive ductal carcinoma, NOS Micropapillary carcinoma | High grade invasive ductal carcinoma, NOS | High grade invasive ductal carcinoma, NOS Metaplastic carcinoma, Medullary carcinoma |

Tumor-infiltrating lymphocytes (TAMs) are white blood cells that have left the bloodstream and migrated towards a tumor. They include T cells and B cells and are part of the larger category of 'tumor-infiltrating immune cells' which consist of both mononuclear and polymorphonuclear immune cells, (i.e., T cells, B cells, natural killer cells, macrophages, neutrophils, dendritic cells, mast cells, eosinophils, basophils, etc.) in variable proportions. Their abundance varies with tumor type and stage and in some cases relates to disease prognosis Necrosis is a form of cell injury which results in the premature death of cells in living tissue by autolysis.

Anisokaryosis corresponds to an inequality in the size of the nuclei of cells.

In an embodiment, the invention concerns a computer-implemented method for identifying at least one class, optionally a biological class, of at least one biological image, comprising the following steps:

- dividing the image into sub-images, called tiles,
- encoding each tile or each selected tile, via a pre-trained model, for example via a pre-trained convolutional neural network, to obtain a representation vector or tensor for each tile concerned,
- assigning a score, also called attention score, to each tile,
- generate a global representation vector or tensor by aggregating all the vectors or tensors of each concerned tile, taking into account the aforementioned scores, for instance through a weighted sum of said vectors or tensors of the tiles, where the weight is the corresponding score of the vector or tensor of said tile,
- determining the class to which the image or at least a part of the image belongs, from the global representation vector or tensor, using a decision model, for example using a pre-trained neural network, for example of the fully connected type.

In a preferred embodiment, an optional step of selecting at least some of the tiles from the set of tiles, for example by removing the background tiles is present, for example between the first step of dividing and the first step of encoding.

In a preferred embodiment, the class is the genomic signature or profile of the cancer, or a molecular class of cancer, in particular selected from triple negative breast cancer or luminal breast cancer, or the class is selected from the cancer's Grade, or from the gBRCA1/2 status, in particular sporadic or germinal cancer, or from the homologous recombination status of a cancer, in particular breast cancer.

In an embodiment of the invention, it is provided a computer-implemented method for classifying an image comprising the following steps:

- dividing the image into sub-images, called tiles,
- encoding each tile or each selected tile, via a pre-trained model, for example via a pre-trained convolutional neural network, to obtain a representation vector or tensor for each tile concerned
- assigning a score, also called attention score, to each tile,
- generate a global representation vector or tensor by aggregating all the vectors or tensors of each concerned tile, taking into account the aforementioned scores, for instance through a weighted sum of said vectors or tensors of the tiles, where the weight is the corresponding score of the vector or tensor of said tile,
- classifying the image or at least a part of the image, from the global representation vector or tensor, using a decision model, for example using a pre-trained neural network, for example of the fully connected type.

In a preferred embodiment, a step of selecting at least some of the tiles from the set of tiles, for example by removing the background tiles is present, for example between the first step of dividing and the first step of encoding.

In a preferred embodiment, the pre-trained model of the encoding step is trained using a self-supervised algorithm, for example using a momentum contrast method.

In a preferred embodiment of the invention, it is provided a method wherein the biological class of the biological image of a cancer tissue obtained from a subject is identified, optionally wherein the class is the genomic signature or profile of the cancer tissue, optionally wherein the class is the homologous recombination (HR) status of the cancer tissue (i.e., homologous recombination deficient (HRD) or non HR deficient ((non HRD) or HR proficient (HRP)), the molecular class and/or the molecular grade, optionally wherein the cancer is breast cancer.

In a preferred embodiment of the invention, it is provided a method wherein the biological class is the genomic tumor (or cancer) profile, notably the Homologous Recombination Deficient (HRD) profile, in particular defined by the presence of a germline BRCA1/2 (gBRCA1/2) mutation or assessed by the Large-scale State Transitions (LST) genomic signature (or LST high) according to Popova et al (14)) or the Homologous Recombination Proficient (HRP) profile, in particular defined as LST low.

In a preferred embodiment of the invention, it is provided a method wherein the neural network is specifically pre-trained on a set of images or sub-images, optionally on a set of images, preferably whole slide images, of a cancer tissue obtained from one or more subjects to classify slide representations between HRD and non-HRD, optionally between HRD and HRP, to the individual tile representations.

In a preferred embodiment of the invention, it is provided a method wherein the images of sub-images are of known class, optionally of known genomic status, optionally of known HR status (HRD or non HRD).

In a preferred embodiment of the invention, it is provided a method wherein when training at least one of the aforementioned models, at least one bias is corrected, for example a bias related to the technique for obtaining the slide represented by said image, for example the fixing technique and/or the impregnation technique, and/or a bias related to a molecular subtype or a molecular class of cancer.

In an embodiment of the invention, it is provided a computer-implemented method for visualizing clusters of sub-images or tiles of at least one biological image, comprising the following steps:

- dividing the image into sub-images or tiles,
- encoding each tile or each selected tile, via a pre-trained model, for example via a pre-trained convolutional neural network, so as to obtain a representation vector or tensor for each tile;
- projecting the tile representation of said tiles or said selected tiles to a low dimensional space, for example a 2-dimensional or 3-dimensional space, for example by using the U-MAP or T-SNE algorithm.

In a preferred embodiment, it is provided a computer-implemented method for visualizing clusters of sub-images or tiles of at least one biological image, comprising the following steps:

- dividing the image into sub-images or tiles,
- selecting at least some of the tiles from the set of tiles, for example by removing the background tiles
- encoding each tile or each selected tile, via a pre-trained model, for example via a pre-trained convolutional neural network, so as to obtain a representation vector or tensor for each tile;
- projecting the tile representation of said tiles or said selected tiles to a low dimensional space, for example a 2-dimensional or 3-dimensional space, for example by using the U-MAP or T-SNE algorithm.

In a preferred embodiment, it is provided a computer-implemented method for visualizing clusters of sub-images or tiles of at least one biological image, comprising the following steps:

- dividing the image into sub-images or tiles,
- encoding each tile or each selected tile, via a pre-trained model, for example via a pre-trained convolutional neural network, so as to obtain a representation vector or tensor for each tile;
- assigning a score, also called attention score, to each tile,
- projecting the tile representation of said tiles or said selected tiles to a low dimensional space, for example a 2-dimensional or 3-dimensional space, for example by using the U-MAP or T-SNE algorithm.

In a preferred embodiment, it is provided a computer-implemented method for visualizing clusters of sub-images or tiles of at least one biological image, comprising the following steps:

- dividing the image into sub-images or tiles,
- encoding each tile or each selected tile, via a pre-trained model, for example via a pre-trained convolutional neural network, so as to obtain a representation vector or tensor for each tile;
- selecting tiles based on the attention score, for example by selecting the tiles with the highest attention scores
- projecting the tile representation of said tiles or said selected tiles to a low dimensional space, for example a 2-dimensional or 3-dimensional space, for example by using the U-MAP or T-SNE algorithm.

In a preferred embodiment, it is provided a computer-implemented method for visualizing clusters of sub-images or tiles of at least one biological image, comprising the following steps:

- dividing the image into sub-images or tiles,
  - encoding each tile or each selected tile, via a pre-trained model, for example via a pre-trained convolutional neural network, so as to obtain a representation vector or tensor for each tile;
- assigning a score, also called decision score, to each tile, for example by predicting the output class from each individual tile
- projecting the tile representation of said tiles or said selected tiles to a low dimensional space, for example a 2-dimensional or 3-dimensional space, for example by using the U-MAP or T-SNE algorithm.

In a preferred embodiment, it is provided a computer-implemented method for visualizing clusters of sub-images or tiles of at least one biological image, comprising the following steps:

- dividing the image into sub-images or tiles,
- encoding each tile or each selected tile, via a pre-trained model, for example via a pre-trained convolutional neural network, so as to obtain a representation vector or tensor for each tile;
- further selecting tiles, as to keep only tiles that have both a high attention and a high decision score
- projecting the tile representation of said tiles or said selected tiles to a low dimensional space, for example a 2-dimensional or 3-dimensional space, for example by using the U-MAP or T-SNE algorithm.

In a preferred embodiment, it is provided a computer-implemented method for visualizing clusters of sub-images or tiles of at least one biological image, comprising the following steps:

- dividing the image into sub-images or tiles,
- optionally selecting at least some of the tiles from the set of tiles, for example by removing the background tiles
- encoding each tile or each selected tile, via a pre-trained model, for example via a pre-trained convolutional neural network, so as to obtain a representation vector or tensor for each tile;
- optionally, assigning a score, also called attention score, to each tile,
- optionally, selecting tiles based on the attention score, for example by selecting the tiles with the highest attention scores
- optionally, assigning a score, also called decision score, to each tile, for example by predicting the output class from each individual tile
- optionally, further selecting tiles, as to keep only tiles that have both a high attention and a high decision score
- projecting the tile representation of said tiles or said selected tiles to a low dimensional space, for example a 2-dimensional or 3-dimensional space, for example by using the U-MAP or T-SNE algorithm.

In a preferred embodiment, it is provided a method which further comprises the following steps:

- identify clusters of tile representations in the low dimensional space,
- label at least part of said clusters and/or identify a feature, or a combination of features or pattern(s) in the tiles belonging to at least part of said clusters.

The present invention also concerns a computer-implemented method for identifying a phenotypical feature, or a combination of phenotypical features or phenotypical pattern in a biological image from a subject, wherein said image is examined for assessing the presence of said phenotypical feature or combination of phenotypical features or phenotypical pattern(s) as defined at the step of labelling of the method, and optionally wherein the phenotypical feature is a histopathological feature.

In a preferred embodiment, it is provided a method wherein the biological image is a whole slide image (WSI), or a portion thereof, for example a tile derived from a WSI.

In a preferred embodiment, it is provided a method wherein the image is a visual representation of a body part using a medical technology imaging such as radiology, magnetic resonance imaging, ultrasound, endoscopy, elastography, tactile imaging, thermography, medical photography, nuclear medicine functional imaging techniques as positron emission tomography (PET) and single-photon emission computed tomography (SPECT).

In a preferred embodiment, it is provided a method wherein the image is an image obtained from a tissue of a subject, notably a whole slide image obtained from a tissue of a subject, or an image of a (histo)pathology section, notably digitized image of (histo)pathology section.

In a preferred embodiment, it is provided a method wherein the tissue is a cancer, or tumor, tissue.

In a preferred embodiment, it is provided a method wherein the tissue is derived from a biopsy obtained from the subject, for example a cancer or tumor biopsy, notably biopsy obtained from a needle biopsy, an endoscopic biopsy, or a surgical biopsy.

In a preferred embodiment, it is provided a method wherein the cancer or tumor is selected from cancers or tumors deficient in homologous recombination (HRD).

In a preferred embodiment, it is provided a method wherein the cancer is selected from breast cancers, ovarian cancers, liver cancers, esophageal cancers, lung cancers, head and neck cancers, prostate cancers, colon, rectal, or colorectal cancers, and pancreatic cancers, preferably breast cancers, ovarian cancers, pancreatic cancers and prostatic cancers.

In a preferred embodiment, it is provided a method wherein the cancer or tumor is a primary or a metastatic cancer or tumor, notably wherein the cancer or tumor is primary ovarian or breast cancer or metastatic pancreatic or prostatic cancer.

In a preferred embodiment, it is provided a method wherein the breast cancer is a luminal (luminal A or luminal B) breast cancer, a triple-negative/basal-like breast cancer (TNBC), an HER2-enriched breast, or a normal-like breast cancer, preferably the breast cancer is a luminal A or luminal B breast cancer.

In a preferred embodiment, it is provided a method wherein the training set of images or sub-images is obtained from a set of biological images, optionally from one or more subjects, optionally of one type of cancer, optionally of one molecular type of cancer (notably of luminal breast cancers), optionally of the same type of tissue or biopsy (notably of breast cancer biopsies).

In a preferred embodiment, it is provided a method wherein the training set of images are stratified in sub groups according to various technical features, including in a non-limitative manner, the type of image (preferably whole slide images), the type of staining, the type of tissue fixation, and/or biological features including in non-limiting manner (the sex of the subject, the age of the subject, the type of cancer, notably the molecular sub-type of cancer, the nature of cancer (e.g., primary or metastatic cancer).

In a preferred embodiment, it is provided a method wherein when training the neural network, confounding effect(s), associated with one or more technical features and/or with one or more biological features of the (training) set of images are assessed according to the method illustrated in FIG. 2 of the results (and associated materials and methods).

In a preferred embodiment, it is provided a method wherein sampling of the training set of images or of the set of tiles is performed before the training of the neural network.

In a preferred embodiment, it is provided a method wherein subgroups of images are selected for specific training of the neural network, optionally wherein the images are whole slide images from stained histopathological section of luminal and triple-negative breast cancers, preferably of luminal breast cancer, optionally wherein the histological sections are stained with Hematoxylin Eosin (HE).

The present invention also concerns a method for identifying the cancer class of an image from a subject comprising the following steps:

- dividing the image into sub-images, called tiles,
- encoding each tile or each selected tile, via a pre-trained model, for example via a pre-trained convolutional neural network, to obtain a representation vector or tensor for each tile concerned
- assigning a score, also called attention score, to each tile,
- generate a global representation vector or tensor by aggregating all the vectors or tensors of each concerned tile, taking into account the aforementioned scores, for instance through a weighted sum of said vectors or tensors of the tiles, where the weight is the corresponding score of the vector or tensor of said tile,
- classifying the image or at least a part of the image, from the global representation vector or tensor, using a decision model, for example using a pre-trained neural network, for example of the fully connected type; wherein the pre-trained model is trained as defined in the previous claims, notably with a training set of images of known cancer class(es), wherein the image of the subject is a whole slide image obtained from a cancer biopsy of said subject, wherein the images of the training set are whole slide images from cancer biopsies, optionally wherein the cancer is selected from breast cancers, ovarian cancers, liver cancers, esophageal cancers, lung cancers, head and neck cancers, prostate cancers, colon, rectal, or colorectal cancers, and pancreatic cancers, preferably breast cancers, ovarian cancers, pancreatic cancers and prostatic cancers, preferably the cancer is breast cancer, notably luminal breast cancer; optionally wherein the WSI are obtained from fixed HE-stained histological sections;

optionally wherein the cancer is breast cancer, optionally wherein the class is the HR status, in particular HRD, or HRP, the molecular class (triple negative/luminal), the cancer's grade, or the gBRCA1/2 status, in particular sporadic or germinal cancer.

In a preferred embodiment, a step of selecting at least some of the tiles from the set of tiles, for example by removing the background tiles is present, for example between the dividing step and the encoding step.

The present invention also concerns a method of stratifying, or classifying a patient comprising the following steps:

- assessing a biopsy image from the patient, optionally a WSI
- dividing the image into sub-images, called tiles,
- encoding each tile or each selected tile, via a pre-trained model, for example via a pre-trained convolutional neural network, to obtain a representation vector or tensor for each tile concerned
- assigning a score, also called attention score, to each tile,
- generate a global representation vector or tensor by aggregating all the vectors or tensors of each concerned tile, taking into account the aforementioned scores, for instance through a weighted sum of said vectors or tensors of the tiles, where the weight is the corresponding score of the vector or tensor of said tile, classifying the image or at least a part of the image, from the global representation vector or tensor, using a decision model, for example using a pre-trained neural network, for example of the fully connected type classifying the patient based at least on the classification of the biopsy image wherein the pre-trained model is trained as defined in the previous claims, notably with a training set of images of known cancer class(es), optionally wherein the class is the HR status, in particular HRD, or HRP and the patient is classified as having a HRD or HRP cancer, wherein the image of the subject is a whole slide image obtained from a cancer biopsy of said subject, wherein the images of the training set are whole slide images from cancer biopsies, optionally wherein the cancer is selected from breast cancers, ovarian cancers, liver cancers, esophageal cancers, lung cancers, head and neck cancers, prostate cancers, colon, rectal, or colorectal cancers, and pancreatic cancers, preferably breast cancers, ovarian cancers, pancreatic cancers and prostatic cancers, preferably the cancer is breast cancer, notably luminal breast cancer.

In a preferred embodiment, a step of selecting at least some of the tiles from the set of tiles, for example by removing the background tiles, is present, for example between the dividing step and the encoding step.

In a preferred embodiment, the WSI are obtained from fixed HE-stained histological sections.

The present invention also concerns an ex vivo method for classifying a patient having a cancer, in particular a breast cancer, according to its homologous recombination status, comprising identification in a tissue section, preferably stained and more preferably HE stained, of a cancer biopsy or of a digitized image therefore, such as a WSI, of one or more of the following histopathological features:

Tumor cell density; HRD tumors present a high tumor cells density; HRP tumors (or non-HRD tumors) present a low tumor cells density; HRP tumors (or non-HRD tumors) present few invasive lobular carcinomas;

Tissue or cell morphology; HRP tumors (or non-HRD tumors) present tumor cell nests separated from the stroma by clear spaces; HRP (or non-HRD tumors) tumors present clear spaces surrounding apocrine cell nests; HRD tumors present basal or hyperchromatic carcinomatous cells, in particular with moderate to high atypia; HRP tumors (or non-HRD tumors) present cells moderately atypical;

Nucleus/cytoplasm ratio; HRD tumors present a high nucleus/cytoplasm ratio; in particular HRD tumor cells present a conspicuous nucleoli;

haemorrhagic suffusion; HRD tumors present a haemorrhagic suffusion, in particular associated with necrotic tissue;

necrotic tissue; HRD tumors present necrotic tissue;

fibrosis; HRD tumors present laminated fibrosis, in particular intra-tumoral laminated fibrosis;

Tumor-Infiltrating Lymphocytes (TILs); HRD tumors present a high content of TILs;

Adipose tissue; HRD tumors may present inflamed adipose tissue, for example adipose tissue intermingled, in particular with scattered and/or clear tumor cells, and/or histiocytes, and/or plasma cells.

Identifying one or more of features, preferably at least 2, 3, 4, 5 or 6 of these features in the tissue section of the cancer biopsy or in the image thereof is indicative of a HRD cancer or a HRP cancer, depending on the histopathological features. These features may be analysed according to the methods and results illustrated in the working examples of the inventions, in particular in examples 3 and FIGS. 3-4.

These histopathological features are known by the skilled artisan, for example an histopathologist, and each of these features may be characterized by the skilled artisan according to methods known from the art.

Assessing one or more, more preferably all, of the above-detailed histopathological features may performed to perform the following methods:

A method for classifying a cancer, in particular a breast cancer, according to the HR status of tumor cells;

A method for discriminating patients having a cancer, in particular a breast cancer, with a HRD status from patients having a cancer, in particular a breast cancer, with a HRP status (or non (HRD status);

A method for selecting a patient having a cancer, in particular a breast cancer, with a HRD status;

A method for selecting a patient having a cancer, in particular a breast cancer, with a HRP status;

A method for treating a patient comprising a step of classifying the patient into either a patient having a cancer, in particular a breast cancer, with a HRD status or a patient having a cancer, in particular a breast cancer, with a HRP status;

The present invention also concerns an ex vivo method for classifying cancers according to their HR status comprising identification in a tissue section, preferably stained and more preferably HE stained, of a cancer biopsy or of a digitized image therefore, such as a WSI, of one or more of the following histopathological features:

a. necrosis
b. high density of tumor associated lymphocytes
c. high nuclear anisokaryosis
d. carcinomatous cells having clear cytoplasm
e. fibrosis, notably intra-tumoral laminated fibrosis,
f. adipose tissue,
g. low tumor cell density,
h. cells being moderately atypical and tumor cell nests separated from the stroma by clear spaces, notably, inclusion of a few invasive lobular carcinomas, wherein identification of one or more of features a to f, preferably at least 2, 3, 4, 5 or 6 of these features in the tissue section of the cancer, in particular the breast cancer, biopsy or in the image thereof is indicative of a HRD cancer, in particular luminal HRD cancer; optionally wherein the presence of at least carcinomatous cells having clear cytoplasm, fibrosis, notably intra-tumoral laminated fibrosis, adipose tissue and combination(s) thereof is indicative of luminal Breast cancer with an HR status (HRD breast cancer);

wherein identification of one or more of features g or h, preferably at least 2 of these features in the tissue section of the cancer, in particular the breast cancer, biopsy or in the image thereof is indicative of a HRP cancer, in particular a HRP breast cancer, more particularly of a HRP luminal breast cancer.

These histopathological features are known by the skilled artisan, for example an histopathologist, and each of these features may be characterized by the skilled artisan according to methods known from the art.

In a particular embodiment, the patient suffers from a breast cancer.

The present invention also concerns a method of treating a patient suffering from a cancer comprising the steps of:

a1. classifying or stratifying the patient according to the method of the invention, optionally wherein the patient is classified or stratified as having an HRD or HRP cancer, or a2.1. identifying a phenotypical feature, or a combination of phenotypical features or phenotypical pattern in a biological image from a subject, and a2.2. classifying or stratifying the patient based on the phenotypical feature, or combination of phenotypical features or phenotypical pattern identified in the biological image of said patient as having an HRD or HRP cancer, or a3. Classifying or stratifying the cancer, in particular the breast cancer, tissue section r image therefore of a patient as HRD or non HRD according to the method of the invention and stratifying the patient based on the classification of said cancer, in particular the breast cancer, tissue section or image thereof b. administering (or recommending or prescribing) an adapted treatment regimen based on the patient stratification.

In a particular embodiment, the patient suffers from a breast cancer.

In a preferred embodiment the method for treating a patient further comprises:

a. when the patient is classified as having an HRD cancer, a cancer treatment selected from a DNA damaging agent, a synthetic lethality agent (e.g., a PARP inhibitor), radiation, or a combination thereof is prescribed or recommended, b. when the patient is classified as having an HRP cancer, recommending or prescribing) a treatment regimen not comprising the use of a DNA damaging agent, a PARP inhibitor, radiation, or a combination thereof; optionally the treatment regimen comprises one or more of a taxane agent (e.g., doxetaxel, paclitaxel, abraxane), a growth factor or growth factor receptor inhibitor (e.g., erlotinib, gefitinib, lapatinib, sunitinib, bevacizumab, cetuximab, trastuzumab, panitumumab), and/or an antimetabolite agent (e.g., 5-flourouracil, methotrexate);

In a preferred embodiment the method is for treating a patient having a breast cancer, In a preferred embodiment the patients are treatment naïve patients.

The present invention also concerns a method of predicting patient eligibility to a cancer treatment comprising the steps of:

a1 classifying or stratifying the patient according to the method of stratifying, or classifying a patient disclosed here above, optionally wherein the patient is classified or stratified as having an HRD or HRP cancer, or a2.1. identifying a phenotypical feature, or a combination of phenotypical features or phenotypical pattern in a biological image from a subject, and a2.2. classifying or stratifying the patient based on the phenotypical feature, or combination of phenotypical features or phenotypical pattern identified in the biological image of said patient as having an HRD or HRP cancer, or a3. Classifying or stratifying the breast cancer tissue section r image therefore of a patient as HRD or non HRD according to the method of the invention and stratifying the patient based on the classification of said breast cancer tissue section or image thereof b. assessing the eligibility of the patient for a given cancer treatment based on the patient classification, optionally wherein:

when the patient is classified as having an HRD cancer, the patient is predicted to be eligible, or responsive to a cancer treatment selected from a DNA damaging agent, a synthetic lethality agent (e.g., a PARP inhibitor), radiation, or a combination thereof, and when the patient is classified as having an HRP cancer, the patient is predicted to be non-eligible or non-responsive to a cancer treatment selected from a DNA damaging agent, a synthetic lethality agent (e.g., a PARP inhibitor), radiation, or a combination thereof;

In a particular embodiment, the patient has a breast cancer.

In a preferred embodiment, DNA damaging agents include, without limitation, inhibitors of poly ADP ribose polymerase, platinum-based chemotherapy drugs (e.g., cisplatin, carboplatin, oxaliplatin, and picoplatin), anthracyclines (e.g., epirubicin and doxorubicin), topoisomerase I inhibitors (e.g., campothecin, topotecan, and irinotecan), DNA crosslinkers such as mitomycin C, and triazene compounds (e.g., dacarbazine and temozolomide).

In a preferred embodiment, synthetic lethality therapeutic approaches typically involve administering an agent that inhibits at least one critical component of a biological pathway that is especially important to a particular tumor cell's survival, in particular PARP inhibitors.

The present invention also concerns a method for determining the prognosis of a patient suffering from a cancer comprising the steps of:

a1. classifying or stratifying the patient as having an HRD or a non HRD (or HRP) cancer according to the method of the invention or, a2.1. identifying a phenotypical feature, or a combination of phenotypical features or phenotypical pattern in a biological image from a subject, and a2.2. classifying or stratifying the patient based on the phenotypical feature, or combination of phenotypical features or phenotypical pattern identified in the biological image of said patient as having an HRD or HRP cancer, or a3. Classifying or stratifying the cancer tissue section r image therefore of a patient as HRD or non HRD according to the method of the invention and stratifying the patient based on the classification of said cancer tissue section or image thereof b1. determining, based at least in part on the classification of the patient as having an HRD cancer, that the patient has a relatively good prognosis, or b2. determining, based at least in part on the classification of the patient as having a non HRD cancer, that the patient has a relatively poor prognosis, optionally wherein the patient prognosis includes the patient's likelihood of survival (e.g., progression-free survival, overall survival), wherein a relatively good prognosis would include an increased likelihood of survival as compared to some reference population (e.g., average patient with this patient's cancer type/subtype, average patient not having an HRD signature, etc.). Conversely, a relatively poor prognosis in terms of survival would include a decreased likelihood of survival as compared to some reference population (e.g., average patient with this patient's cancer type/subtype, average patient having an HRD signature, etc.).

In a particular embodiment, the patient suffers from a breast cancer.

In the present application, we set out to predict the HR status in breast cancer from H&E stained WSI and to analyse the phenotypic patterns related to HRD. The prediction of HRD is an important challenge in clinical practice. The use of PARP inhibitors for breast cancer patients was initiated for metastatic TNBC patients with germline mutations of BRCA1 or BRCA2. However, BRCA2, as well as PALB2 and a minority of BRCA1 cancer patients, develop luminal tumors. The necessity of predicting HRD is therefore not limited to TNBC, but extends also to luminal BC. On the other hand, luminal BCs represent a far more frequent group than TNBC. For this reason, systematic screening of HR gene alterations for luminal cancers will be problematic and, in many countries, even infeasible due to both economic and logistic issues. Therefore, preselection of patients with a high probability of being HR deficient by analysis of WSI is a cost-efficient strategy that has so far only been hampered by the lack of knowledge about HRD specific morphological patterns in luminals. Indeed, only high grades and to a lower extent pushing margins have previously been reported to be associated with HRD. In this context, the identification of HRD from WSI by deep learning and the identification of related morphological patterns could both facilitate the preselection of breast cancers for molecular determination of HRD, which is particularly important for luminal cancers.

The TCGA provides a precious data set to train models for the prediction of genetic signatures from H&E data[5,8]. While we obtained promising results for the prediction of HRD on the TCGA dataset in line with previous reports, we found that this result was partly due to the fact that the molecular subtype acts as a biological confounder. This was particularly problematic as we wanted to investigate the morphological signature of HRD. Of note, the existence of biological and technical confounders is presumably not limited to HRD prediction, but may concern many genetic signatures. The use of carefully curated data sets where technical and biological confounders can be controlled for, is thus an important step in investigating the predictability of genetic signatures, as well as the identification of their morphological counterparts.

In most cases, such in-house datasets also contain technical and biological biases, due to the long period during which the dataset is acquired. This motivated us to propose a method to mitigate bias in Computational Pathology workflows, based on strategic sampling. Such strategies are already used in other fields of biomedical imaging but have so far-to the best of our knowledge—not been used in Computational Pathology. We have shown that this approach can successfully mitigate or even eliminate bias. However, the method is limited by the number of variables we can correct for, as well as by the class imbalance it can handle. In some cases, stratification might therefore be preferable. In any case, it is important to be aware of the confounding variables in the data set, whose presence can lead to false expectations and misinterpretation. For this reason, we expect proper treatment of such variables to become a standard in the field.

While bias correction on the TCGA led to a drop in AUC to 0.63, we found that HRD was predictable in our in-house data set of 715 BC patients with an AUC of 0.83. While homogeneous datasets do not reflect the variability between centres and thus limit direct applicability of the trained networks, they allow for controlled feasibility studies, which now need to be complemented by multicentric studies. In addition, we will validate this algorithm in a prospective neoadjuvant clinical trial for which patients' HRD status will be assessed with MyChoice® CDx test (Myriad).

Homogeneous datasets are well suited for the identification of phenotypic patterns linked to disease patterns, even in cases where no such patterns are known a priori, such as in the case for HRD. In order to identify a phenotypic signature related to an output variable (here HRD), we can either use biologically meaningful encodings, also known as human interpretable features (HIF), and infer the most relevant features by analyzing the weights in the predictive model 8, or we can turn to network introspection. The HIF approach relies on detailed and exhaustive annotations of a large number of WSI. For instance, 8 leverage annotations provided by hundreds of pathologists consisting of hundreds of thousands of manual cell and tissue classifications. Here, we provide a new network introspection scheme, relying on the powerful MoCo encodings, trained without supervision directly on histopathology data, and a decision-based tile selection, that allows us to automatically cluster tiles and to relate these clusters to the output variable.

Interestingly, while our approach confirms the recently published finding that necrosis is a hallmark of HRD[8] and identifies morphological features common to HRD in TNBC and luminal BC, such as necrosis, high density in TILs and high nuclear anisokaryosis[39], it also points to more specific patterns that have so far been overlooked. For instance, we found tiles enriched in carcinomatous cells with clear cytoplasm suggesting activation of specific metabolic processes in these cells. Second, we find intra-tumoral laminated fibrosis as an HRD related pattern. This suggests the hypothesis that cancer-associated fibroblast (CAF) within the stroma of HRD luminal tumors may play a role in the viability and fate of tumor cells. Furthermore, the presence of adipose tissue within the tumor suggests first a different tumor cell density and second a specific balance between CAF and adipocytes in the context of a luminal HRD tumor. The molecular mechanisms achieving these patterns remain to be determined by in vitro models.

Similar to what we have shown here with respect to HRD, the visualization framework we have developed is versatile and can in principle be applied in the context of other genetic signatures. Because the algorithm is fully automated, using the MIL algorithm and its visualization method can constitute a useful tool for the discovery of morphological features related to the predicted genetic signatures. This has the potential to generate new biological hypotheses on the phenotypic impact of these genetic disorders. In order to maximize the benefit for the scientific community, we release the code to train MIL models on WSIs and to create morphological maps as well as tile trajectories publicly and free of charge, and provide detailed documentation. Altogether, this study provides new and versatile tools for the prediction and phenotypic dissection of genetic signatures from histopathology data. Application to luminal breast cancers allowed us to shed light on the phenotypic consequences of homologous recombination deficiency, and might provide a tool with the potential to impact breast cancer patient care.

BRIEF DESCRIPTION OF THE DRAWINGS

FIG. 1. Illustrative scheme of a method starting from Whole slide images to prediction. Four major components are used in this end-to-end pipeline. First, the WSI (X) are tiled, the tissue parts are automatically selected, and the resulting tiles are embedded into a low-dimensional space (block 1). The embedded tiles are then scored through the attention module (2). An aggregation module outputs the slide level vector representative (3) that is finally fed to a decision module (4) that outputs the final prediction. When training, the binary cross-entropy loss between the ground truth y and the prediction is computed and back-propagated to update the parameters of the modules. Both the decision module and the attention module are multi-layer perceptrons, the encoder is a ResNet18 and the aggregation module consists of a weighted sum of the tiles, the weights being the attention scores.

METHODS

Figure 2:
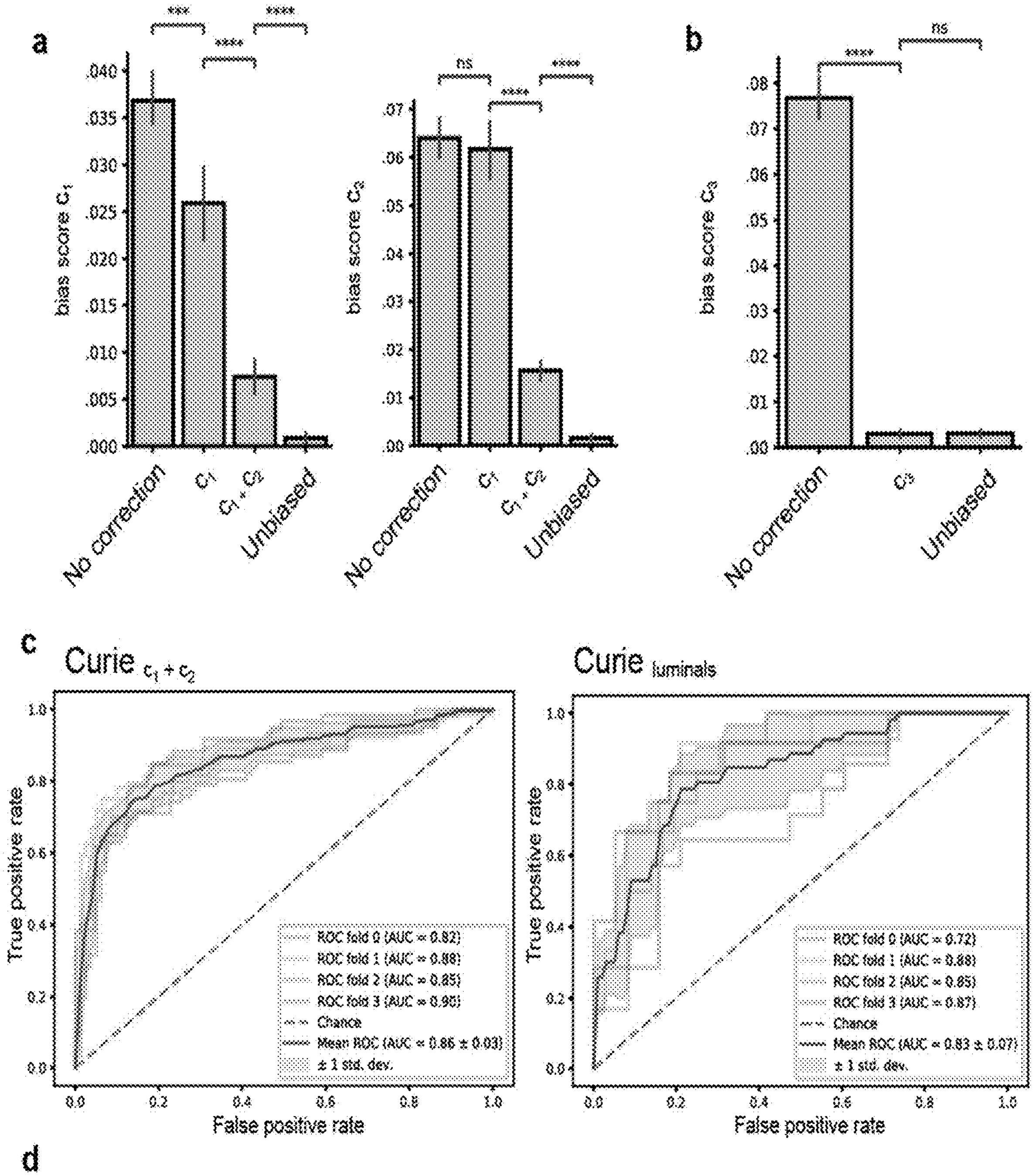
FIG. 2. Bias corrections and prediction performances. a-b: estimation of the bias score of two technical confounder (C1, C2) and one biological confounder (C3) for the Curie Dataset (a) and the bias score of the confounder Cs for the TCGA dataset (b) for different correction strategies. A Mann-Whitney-Wilcoxon test two-sided with Bonferroni correction is performed for each pair of correction strategies. ns: non-significant p>0.05, *: p<0.05, : p<0.01, *: p<1e-3, **: p<1e-4. c-d: performance results. Name of each model indicates the origin of its training set. Indices indicate the correction applied through strategic sampling (Curieci has been debiased with respect to C1). Curie$_{luminals}$ corresponds to the model trained on a subset containing only luminal tumors. c: ROC curve of the models trained on the Curie dataset correcting for technical bias (Curie$_{C1}$) or for technical biases and $C_3$ (Curie$_{luminals}$). d: summary tables of performance metrics. AUC: Area Under The (receiver operating characteristics) Curve, $B_{Acc}$: balanced accuracy FIG. 3**. Attention- and Decision-based visualizations. I) Attention-based visualization does not discriminate between HRD and HRP. a: Mechanism of the attention-based visualization. The attention score of a tile is used as a direct proxy of its importance in the prediction of the WSI. b: UMAP projection of the highest attention ranked tiles of the Curie WSIs classified as HRP (orange crosses) and HRD (blue circles). c: Randomly sampled tiles among the HRP and HRD tiles. The tiles are located in the tumor, however, neither clear clusters nor visual differences are present between HRD and HRP tiles. II) Decision-based visualization. a: Mechanism of the decision-based visualization. 1, Each tile in the whole dataset is scored by the attention module. 2, The best scoring tiles are selected as candidate tiles. 3, The selected tiles are presented to the decision module, the probability of each of these tiles being HRD or HRP (yellow or green) is kept. 4, Finally, the K tiles with maximal probability for either HRD/HRP are selected. b: Morphological map of the HR status. Each dot is the UMAP projection of a tile extracted by the decision-based visualization method. Crosses are tiles with high probability of being HRD; circles are tiles maximizing HRP prediction. Each cluster has been linked to a morphological phenotype by two expert pathologists. We identified six different morphological phenotypes associated with the HRD and two associated with the HRP. The exhibited tiles have been randomly sampled among each cluster. c: Pathological interpretation of the clusters presented in b.

In-house dataset (Institut Curie). We retrospectively retrieved a series of 715 patients with HE slides of surgical resections specimens of untreated breast cancer and a genomically known HR status. The series is composed of 309 Homologous Recombination Proficient tumors (HRP) and 406 Homologous Recombination Deficient tumors (HRD). The HRD status was either identified by the presence of a germline BRCA1/2 (gBRCA1/2) mutation or assessed by LST genomic signature according to Popova et al. for the sporadic triple-negative and luminal cancers.

All patients have been treated and followed at the Institut Curie between 1995 and 2020. The patient agreed for the use of tumor samples from their surgical resection specimens for research according to the law. Ethical approval from the Institutional Review Board (Institut Curie breast cancer study group N°DATA190031) was obtained for the use of all specimens. Clinical data have been retrieved from the Institut Curie electronic medical records and saved using Research electronic data capture (REDCap) tools hosted at the Institut Curie.

Public dataset (TCGA). This public dataset is composed of 815 WSI of breast cancer fixed in formalin (FFPE) and stained in H&E. They are available at https://portal.gdc.cancer.gov/. Low-resolution WSI, WSI containing artifacts such as pen marks, tissue-folds and blurred WSI were removed. The final dataset encompasses 691 WSIs. The HR status of the corresponding tumors was obtained using the LST genomic signature[14].

Architecture and optimization parameters. Hyperparameters have been set thanks to a random search evaluated through 5-fold nested cross-validation. The benchmark task is the prediction of the molecular class of the TCGA WSIs.

Both the decision module and the tile-scoring module are multilayer perceptrons with batch normalization[43] after each hidden layer. The decision module has 3 hidden layers of 512 neurons, the tile-scoring module has 1 hidden layer of 256 neurons. Dropout has been fixed at 0.4, the optimizer is ADAM[44] with a learning rate of 3e-3. A batch consists of 16 samples of WSI. A sample of WSI corresponds to a uniform sampling of 300 of its composing tiles. In fact, we observed that this uniform subsampling of the WSIs regularized training as well as diminishes its computational workload. Finally, training is performed during 200 epochs. Training and performance evaluation are done in a 5-fold nested cross-validation framework. Each dataset is split into 5 independent folds. For each of these folds, a validation set is randomly sampled in the complementary $4/5$th. A model is trained on the remaining dataset ($=4/5*4/5$ th of the total dataset). This process is repeated 10 times for each test fold, then the best model is selected according to its validation performances, and finally tested on its test set. Each test and validation set preserves the stratification of the whole dataset with respect to the target variable as well as the confounding variables in case we correct for them. The final performance estimation of the model is the performance averaged over the 5 test performances. During inference time, all the tiles of each WSI are processed.

Strategic sampling is used both for balancing the training dataset with respect to the output variable ($T=\{t_1,t_2\}$ in the binary case) and to correct for biases ($B=\{b_1, b_2, b_3, \ldots b_n\}$). If X is a given WSI sampled from the dataset, then T(X) and B(X) are respectively the target value and the bias value of X. We note $|t_1|$ the total number of slides in the dataset labeled with t1, same for $|b_i|$. $|t_1|$ is the total number of slides with label value ti and bias value bi. For achieving both, we sample the WSIs X in each batch in a distribution P under which $\mathcal{P}(\{T(X)=t_1\})=\mathcal{P}(\{T(X)=t_2\})$ and $\mathcal{P}(\{T(X)=t_1\}\cap\{b(X)=b_i\})=\mathcal{P}(\{T(X)=t_2\}\cap\{b(X)=b_i\})$ for all i.

That is: $\mathcal{P}(X|\{T(X)=t_j\}\cap\{(X)=b_i\})\propto|t_j|/|t_j b_i|$ for each $i\leq n$, $j\leq m$.

Strategic sampling is performed on the fly when building the batches. When correction for several confounder simultaneously, $B=\{b_1, b_2, \ldots, b_n\}$ and $C=\{c_1, c_2, \ldots, c_m\}$, a new confounder variable is created that takes values in all the pairs combinations of $b_i$ and $c_j$:

$$C=\bigcup_{i=1}^{n}\bigcup_{j=1}^{m}\{(b_i, c_j)\}$$

We then apply strategic sampling to correct for C.

Bias Score.

The bias score of a confounder variable is the average mutual information between B and the predicted class c ($I(B_D, C_D)$ estimated in a dataset D in which the mutual information between B and the target T is zero. We sample 30 sub-dataset $D_i$ in the test set using strategic sampling such that $I(B_{D_i}, T_{D_i})=0$ and average over them to get the bias score BS(B):

$$BS(B)=\frac{1}{30}\sum_{i=1}^{30} I(B_{D_i}, C_{D_i}).$$

The mutual information I(B,P) between two finite random variables B and Q taking value respectively in $\{b_1, b_n\}$ and $\{q_1, \ldots, q_m\}$ measures the dependency between B and Q and is defined by:

$$I(B; Q)=\sum_{i\leq n, j\leq m} P(b_i, q_j)\log\frac{P(b_i, q_j)}{P(b_i)P(q_j)}.$$

Because this average is non-negative even when C is not biased (but tends to zero when Di is large), we compute the bias score of an unbiased model predicting the target variable with the same accuracy as the tested model. It serves as a control.

Learning MoCo Representations.

For learning MoCo-v2 representation we used the MoCo repository available at https://github.com/facebookresearch/moco. We randomly used the following transformations: Gaussian blur, crop and resize, color jitter, grayscale, horizontal and vertical symmetries, and finally a color augmentation in the Hematoxylin and Eosin specific space (ref Ruifrok). The training dataset is composed of 5.3e6 images of size 224×224 pixels, or half the Curie dataset at magnification 10×. We used a Resnet18 and trained it for 60 epochs on 4 GPU Nvidia Tesla V100 SXM2 32 Go. We used the SGD optimizer with a momentum of 0.9, a weight decay of 1e-4 and a learning rate of 3e-3. We used a cosine scheduler with warm restart on the learning rate.

Visualization Methods.

The model used to extract the visualizations has been trained on the luminal subset of the Curie dataset (259 WSI). To benefit from the biggest dataset possible, the model has been trained on the whole dataset, without using early stopping nor testing, during 200 epochs. To generate the attention-based visualization, the highest ranked tile with respect to the attention score is extracted, for each WSI. The selected tiles are then labeled according to the label of their WSI of origin.

Concerning the decision-based visualisation, for each WSI the 300 highest ranked tiles with respect to the attention score are selected. Amond this pool of tiles, the 2000 highest ranking tiles with respect to the posterior probability for HRD and HRP are selected. In order to promote diversity in the extracted images, no more than 20 tiles per slide can be selected.

Computation Resources.

All computations have been done on the GENCI HPC cluster of Jean-Zay.

EXAMPLES

Example 1: Deep Learning Architecture to Predict HRD from Whole Slide Images (WSI)—FIG. 1

The most representative HE stained tissue section of the surgical resections specimens of breast cancer from 715 patients with known HR status have been scanned. The series was composed of 309 Homologous Recombination Proficient (HRP) tumors and 406 Homologous Recombination Deficient tumors.

Due to their enormous size, analysis of WSI typically relies on the Multiple Instance Learning (MIL) paradigm[23-26]. MIL techniques only require slide-level annotations and share the overall architecture (see FIG. 1) consisting of 4 main steps: tiling and encoding, tile-scoring, aggregation, and decision.

The WSI was divided into tile images (dimension: 224×224 pixels) arranged in a grid. Background tiles are removed, tissue tiles are encoded into a feature vector. Instead of using representations trained on natural image databases and unlike most studies in this domain, the self-supervised technique Momentum Contrast (MoCo[27]; see Methods) has been used. This method consists in training a Neural Network to recognize images after transformations, such as geometric transformations, noise addition and color changes. By choosing the kind and strength of transformations, invariance classes can be imposed, i.e. variations in the input that do not result in different representations. The feature vector of each tile was then mapped to a score by a neural network. The slide representation was obtained by the sum of the individual tile representations, weighted by the learned attention scores[23]. Finally, the slide representation was classified by the decision module (see FIG. 1). Hyper-parameters has been optimized by a systematic random search strategy (see Methods). For hyperparameter setting and performance estimation, nested 5-fold cross-validation was used, which allows the obtention of realistic performance estimations. All reported performance results are averaged over 5 independent test folds (see Methods).

Example 2: HRD Prediction with Correction for Potential Biases—FIG. 2

The method of example 1 has been applied to predict HRD from the WSI in the TCGA cohort, and results were obtained (AUC=0.71; see FIG. 2.*c*) in line with previous reports (Diao et al. 2021; Kather et al. 2020). While the TCGA is an invaluable resource for pan-cancer studies in genomics and histopathology, it is often seen rather as a starting point whose results need to be corroborated by other cohorts 28. Furthermore, the TCGA contains images from many centres around the world with potentially different sample preparation and image acquisition protocols. While this technical variability might reflect to some degree what could be expected in clinical practice for multiple institutions, it has been hypothesized that to prove the predictability of HRD independently from potential technical and biological biases, as well as an in-depth study of morphological patterns related to HRD, it might be advantageous to work on a more homogeneous data set, where careful control for potential technical and biological confounders can be performed. In-house dataset, the Curie dataset (see Methods), with data from 715 patients has thus been used.

Training a Neural Network (NN) to predict HRD on the raw data set, we observed an important increase in prediction performances, as compared to the TCGA (AUC=0.88; see FIG. 2.*c*). As the cohort was generated over 25 years, two experimental variables (C1, C2, see Methods) representing slight changes in experimental protocols have been identified as potential confounders. To measure the confounding effects of these variables on the model predictions, a bias score has been developed (see methods). This score is close to 0 in the unbiased case. The model predictions were indeed biased by these two confounders (see FIG. 2.*a*).

We then devised a sampling strategy that mitigates biasing during training. Bias mitigation is an increasingly important line of research in machine learning. For instance, it is a well-known problem in training predictive models for functional magnetic resonance imaging (fMRI) data, where the age of the patient has been shown to be an important confounder[29]. While several techniques for bias mitigation exist[30-33], a recent comparison[34] indicates that strategic sampling is the method of choice if the distribution is not too imbalanced. Strategic sampling aims at ensuring that irrespectively of the composition of the training set, each batch presented to the neural network is composed of roughly the same number of samples for each value combination of output and confounding variable. Correcting for $C_1$ and $C_2$ resulted in a 4-fold reduction of the bias-score in comparison to the uncorrected model and a slightly lower accuracy (AUC=0.85, FIG. 2.*c*).

In addition to these technical confounders, the molecular subtype of the tumor to be a potential biological confounder has been identified. Successful correction of this biological confounder in the TCGA (see FIG. 2.*b*) led however to a dramatic drop in performance (AUC=0.63). This result suggests that NN trained on the TCGA for HRD prediction without stratification or bias correction, might actually predict to some extent the molecular subtype, which is also a predictable variable (AUC=0.89). This shows that the molecular subtype is indeed a biological confounder. In the in-house data set, a subtype specific NN that specifically predicts HRD for luminal BC, instead of applying bias mitigation, has been built. The reason for this decision was three-fold: first, we argued that a dataset focusing on only one molecular subtype was more likely to reveal the underlying patterns exclusively related to HRD; second, HRD prediction in luminal BC is of particular importance for clinical practice, as very few morphological patterns are known to be related to HRD in luminal BC, the most frequent breast cancer phenotype, and third, the relatively low number of TNBC in the data set made strategic sampling on three confounding variables challenging. Therefore, we composed a dataset containing only luminal BC and setting both technical confounders, leading us to keep 259 BC WSI(191 HRD tumors, 66 HRP tumors). We obtained a good, albeit slightly lower performance of this bias-corrected NN (AUC=0.83, FIG. 2.*c*; FIG. 2.*d*) which we consider as a realistic score for a homogeneous dataset where biases are either removed or controlled for. The trained model carefully freed from both technical and biological biases was then used for the identification of morphological patterns described in the next example.

Example 3: Visualization Reveals HRD Specific Tissue Patterns—FIGS. 3 and 4

In order to understand which phenotypic patterns are related to HRD on the WSI, we turned to visualization techniques for NN. The used MIL framework is equipped with an inherent visualization mechanism: the second module of the algorithm, the tile-scoring module, is in fact an attention module that assigns to each tile an attention score that determines how much a given tile will contribute to the slide representation (and thus to the decision). Attention scores are often used for visualization in the field of pathology 3.35-37, either in the form of heatmaps in order to localize the origin of the relevant signals or in the form of galleries of tiles of interest (tiles with highest attention scores).

Figure 4:
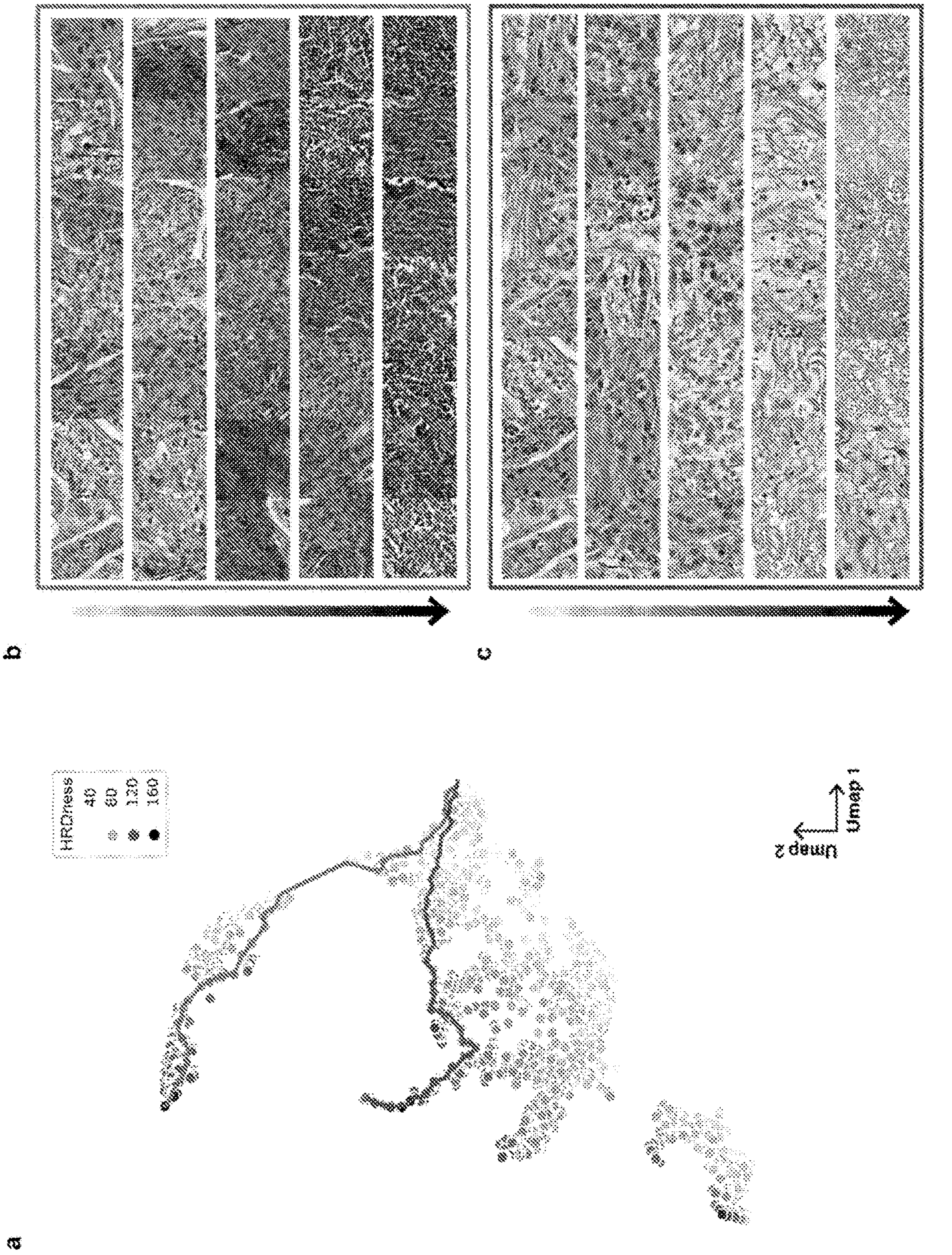
FIG. 4. Illustration of 2 Phenotypic HRD-ness trajectories. A: UMAP projection of the HR status specific representation of the meaningful tiles relative to the HRD. HRD-ness is the score given to each tile by the HRD output neuron. Two tile trajectories have been extracted (blue and magenta) starting from the same low HRD-ness region, each leading to a different high HRD-ness region. B, C: Tiles sampled along each of the trajectories. They are ordered from low HRD-ness to high HRD-ness and read from left to right and from up to bottom. B: Magenta trajectory, toward densely cellular tumors or inflammatory cells. C: Blue trajectory, toward fibroinflammatory tumor changes and haemorrhagic suffusions

However, attention scores do not per se extract the tiles that are related to a certain output variable; they just reflect that the tile is to be taken into consideration in the decision. In particular in the case of genetic signatures, where we would expect that the output variables can be related to several morphological patterns, analysing only the attention scores might be limited. In the case of HRD prediction, this intuition is corroborated by the results presented in FIG. 3: selecting the tiles with the highest attention scores does not allow to identify tiles related to HRD or HRP, respectively. Moreover, a low-dimensional representation, obtained by Uniform Manifold Approximation and Projection (UMAP) [38] of the tile descriptors does not show any grouping that seems to relate to the output variable. Given these limitations, we propose a new visualization protocol that allows us to extract the tiles that are directly associated with a particular slide-level label. As the slide representation is the weighted sum of the tile representations, we applied the decision module, specifically trained to classify slide representations between HRD and HRP, to the individual tile representations. This gives us a score for each tile that can be interpreted as the (tile) probability of being HRD or HRP (see Methods for details). Selecting the tiles with the highest posterior probability for HRD and HRP respectively, and projecting the tile representations of this selection to a low dimensional space leads to the emergence of distinct clusters corresponding to different tumor tissue patterns with a clear relation to HRD or HRP and therefore providing a morphological map of HRD (FIG. 4).

Two expert pathologists labeled these clusters. The HRD signal relied on several clusters: HRD tumors present a high tumor cell density, with a high nucleus/cytoplasm ratio and conspicuous nucleoli. They also show regions of hemorrhagic suffusion associated with necrotic tissue. In the stroma, the HRD signal revealed the presence of striking laminated fibrosis and as expected relied on high Tumor-Infiltrating Lymphocytes (TILs) content. Lastly, one large cluster contained a continuum of several phenotypes, namely adipose tissue intermingled with scattered and clear tumor cells, histiocytes, and plasma cells.

In contrast, the HRP signal was mostly carried by one cluster characterized by low tumor cell density, the cells being moderately atypical and tumor cell nests separated from the stroma by clear spaces. Notably, it included a few invasive lobular carcinomas.

Our approach thus suggests that these tissue phenotypes are hallmarks of HRD. In contrast to triple-negative tumors that have been described as high-grade, rich in TILs, with pushing margins[39], no specific pathological patterns of luminal breast gBRCA 1 or 2 cancers were identified except a high grade with a frequent absence of tubules formation and pushing margins. However, these features did not allow a robust identification of HRD luminal tumors in clinical practice[40-42]. Here, thanks to our visualization tool and our unbiased deep-learning analysis, we identified new features linked to HRD in luminal breast cancers. In order to test this analysis result, the TIL density and nuclear grade were evaluated for each tumor of the in-house dataset by an expert pathologist. As predicted by our algorithm, TILs and nuclear grade were positively associated with the HR status of the tumor in the luminal subset (mean TILs HRD: 29, mean TILs HRP: 17, t-test-pvalue: 0.017; mean nuclear grade HRD: 2.7, mean nuclear grade HRP: 2.3, Xi2-pvalue: 1.2 e-6). Our NN works with different internal representations. While the tile representations provided by MoCo permit the emergence of phenotypic similarity clusters (FIG. 4), internal representations closer to the decision module encode information relevant for HRD. The representation in the penultimate layer can therefore be interpreted as encoding "HRD-ness" of the tiles. FIG. 4 illustrates a low dimensional representation of this HRD-ness for the same tiles as those present in FIG. 4, where point colour represents the HRD-score (tile probability to be classified as HRD). From there, we have extracted two tile trajectories, going from low HRD-ness to high HRD-ness. The magenta trajectory illustrates the successive visual changes corresponding to an increase in tumor cells or inflammatory cells density (from low-density tiles to high-density tiles with large nuclei, nuclear atypia and infiltrative lymphocytes). The blue trajectory shows conversely a decrease in tumor cells density replaced successively by an inflammatory reaction and apoptotic cells, loose fibrosis and haemorrhagic suffusion associated with necrosis. These different trajectories Millustrate the manifestations of HRD and show the pleiotropic character of the induced phenotypes. Moreover, the highlighted gradation of these phenotypes opens the path to a possible reading grid of WSIs for pathologists.

BIBLIOGRAPHIC REFERENCES

1. Veta, M. et al. Assessment of algorithms for mitosis detection in breast cancer histopathology images. Med. Image Anal. 1-23 (2014).
2. Ehteshami Bejnordi, B. et al. Diagnostic Assessment of Deep Learning Algorithms for Detection of Lymph Node Metastases in Women With Breast Cancer. JAMA 318, 2199-2210 (2017).
3. Campanella, G. et al. Clinical-grade computational pathology using weakly supervised deep learning on whole slide images. Nat. Med. 25, 1301-1309 (2019).
4. Mobadersany, P. et al. Predicting cancer outcomes from histology and genomics using convolutional networks. Proc. Natl. Acad. Sci. 115, E2970-E2979 (2018).
5. Kather, J. N. et al. Pan-cancer image-based detection of clinically actionable genetic alterations. Nat. Cancer 1, 789-799 (2020).
6. Coudray, N. et al. Classification and mutation prediction from non-small cell lung cancer histopathology images using deep learning. Nat. Med. 24, 1559-1567 (2018).
7. Schmauch, B. et al. A deep learning model to predict RNA-Seq expression of tumours from whole slide images. Nat. Commun. 11, (2020).
8. Diao, J. A. et al. Human-interpretable image features derived from densely mapped cancer pathology slides predict diverse molecular phenotypes. Nat. Commun. 12, 1613 (2021).
9. Deluche, E. et al. Contemporary outcomes of metastatic breast cancer among 22,000 women from the multicentre ESME cohort 2008-2016. Eur. J. Cancer 129, 60-70 (2020).
10. Miller, R. E. et al. ESMO recommendations on predictive biomarker testing for homologous recombination deficiency and PARP inhibitor benefit in ovarian cancer. Ann. Oncol. Off. J. Eur. Soc. Med. Oncol. 31, 1606-1622 (2020).
11. Bryant, H. E. et al. Specific killing of BRCA2-deficient tumours with inhibitors of poly (ADP-ribose) polymerase. 434, 6 (2005).
12. Farmer, H. et al. Targeting the DNA repair defect in BRCA mutant cells as a therapeutic strategy. Nature 434, 917-921 (2005).
13. Tung, N. M. et al. TBCRC 048: Phase II Study of Olaparib for Metastatic Breast Cancer and Mutations in Homologous Recombination-Related Genes. J. Clin. Oncol. 38, 4274-4282 (2020).
14. Popova, T. et al. Ploidy and Large-Scale Genomic Instability Consistently Identify basal-like Breast Carcinomas with BRCA1/2 Inactivation. Cancer Res. 72, 5454-5462 (2012).
15. Birkbak, N. J. et al. Telomeric Allelic Imbalance Indicates Defective DNA Repair and Sensitivity to DNA-Damaging Agents. Cancer Discov. 2, 366-375 (2012).
16. Abkevich, V. et al. Patterns of genomic loss of heterozygosity predict homologous recombination repair defects in epithelial ovarian cancer. Br. J. Cancer 107, 1776-1782 (2012).
17. Polak, P. et al. A mutational signature reveals alterations underlying deficient homologous recombination repair in breast cancer. Nat. Genet. 49, 1476-1486 (2017).
18. Davies, H. et al. HRDetect is a predictor of BRCA1 and BRCA2 deficiency based on mutational signatures. Nat. Med. 23, 517-525 (2017).
19. Tutt, A. et al. Carboplatin in BRCA1/2-mutated and triple-negative breast cancer BRCAness subgroups: the TNT Trial. Nat. Med. 24, 628-637 (2018).
20. Chopra, N. et al. Homologous recombination DNA repair deficiency and PARP inhibition activity in primary triple negative breast cancer. Nat. Commun. 11,2662 (2020).
21. Manié, E. et al. Genomic hallmarks of homologous recombination deficiency in invasive breast carcinomas: Genomic hallmarks of homologous recombination defect. Int. J. Cancer 138, 891-900 (2016).
22. Holstege, H. et al. BRCA1-mutated and basal-like breast cancers have similar aCGH profiles and a high incidence of protein truncating TP53 mutations. BMC Cancer 10, 654 (2010).
23. Ilse, M., Tomczak, J. M. & Welling, M. Attention-based Deep Multiple Instance Learning. ArXiv180204712 Cs Stat (2018).
24. Amores, J. Multiple instance classification: Review, taxonomy and comparative study. Artif. Intell. 201, 81-105 (2013).
25. Maron, O. & Lozano-Perez, T. A Framework for Multiple-Instance Learning. in Advances in Neural Information Processing Systems (NeurIPS) (eds. Jordan, M. I., Kearns, M. J. & Solla, S. A.) 570-576 (MIT Press, 1998).
26. Courtiol, P., Tramel, E. W., Sanselme, M. & Wainrib, G. Classification and disease localization in histopathology using only global labels: a weakly supervised approach. CoRR 1-13 (2017).
27. He, K., Fan, H., Wu, Y., Xie, S. & Girshick, R. Momentum Contrast for Unsupervised Visual Representation Learning. ArXiv191105722 Cs (2020).
28. Kleppe, A. et al. Designing deep learning studies in cancer diagnostics. Nat. Rev. Cancer 1-13 (2021) doi: 10.1038/s41568-020-00327-9.
29. Varoquaux, G. et al. Assessing and tuning brain decoders: cross-validation, caveats, and guidelines. NeuroImage 145, 166-179 (2017).
30. Zhao, Q., Adeli, E. & Pohl, K. M. Training confounder-free deep learning models for medical applications. Nat. Commun. 11, 6010 (2020).
31. Zhao, J., Wang, T., Yatskar, M., Ordonez, V. & Chang, K.-W. Men Also Like Shopping: Reducing Gender Bias Amplification using Corpus-level Constraints. ArXiv170709457 Cs Stat (2017).
32. Adeli, E. et al. Representation Learning with Statistical Independence to Mitigate Bias. ArXiv191003676 Cs (2020).
33. Wang, T., Zhao, J., Yatskar, M., Chang, K.-W. & Ordonez, V. Balanced Datasets Are Not Enough: Estimating and Mitigating Gender Bias in Deep Image Representations. ArXiv181108489 Cs (2019).
34. Wang, Z. et al. Towards Fairness in Visual Recognition: Effective Strategies for Bias Mitigation, in 2020 IEEE/CVF Conference on Computer Vision and Pattern Recognition (CVPR) 8916-8925 (IEEE, 2020). doi: 10.1109/CVPR42600.2020.00894.
35. Lu, M. Y. et al. Data-efficient and weakly supervised computational pathology on whole-slide images. Nat. Biomed. Eng. 1-16 (2021) doi: 10.1038/s41551-020-00682-w.
36. Dehaene, O., Camara, A., Moindrot, O., de Lavergne, A. & Courtiol, P. Self-Supervision Closes the Gap Between Weak and Strong Supervision in Histology. ArXiv201203583 Cs Eess (2020).
37. Courtiol, P. et al. Deep learning-based classification of mesothelioma improves prediction of patient outcome. Nat. Med. 25, 1519-1525 (2019).
38. McInnes, L., Healy, J. & Melville, J. UMAP: Uniform Manifold Approximation and Projection for Dimension Reduction. ArXiv180203426 Cs Stat (2018).
39. Rakha, E. A., El-Sayed, M. E., Reis-Filho, J. & Ellis, I. O. Patho-biological aspects of basal-like breast cancer. Breast Cancer Res. Treat. 113, 411-422 (2009).
40. Stratton, M. R. Pathology of familial breast cancer: differences between breast cancers in carriers of BRCA1 or BRCA2 mutations and sporadic cases. The Lancet 349, 1505-1510 (1997).
41. Lakhani, S. R. et al. The Pathology of Familial Breast Cancer: Histological Features of Cancers in Families Not Attributable to Mutations in BRCA1 or BRCA2. Clin. Cancer Res. 6, 782 (2000).
42. Bane, A. L. et al. BRCA2 Mutation-associated Breast Cancers Exhibit a Distinguishing Phenotype Based on Morphology and Molecular Profiles From Tissue Microarrays. Am. J. Surg. Pathol. 31, (2007).
43. Ioffe, S. & Szegedy, C. Batch Normalization: Accelerating Deep Network Training by Reducing Internal Covariate Shift. ArXiv150203167 Cs (2015).
44. Kingma, D. P. & Ba, J. ADAM: A Method for Stochastic Optimization. ArXiv14126980 Cs 1 (2017).

The invention claimed is:

1. A computer-implemented method for identifying at least one biological class, of at least one biological image, comprising the following steps:

a. dividing the image into sub-images, called tiles, b. selecting at least some of the tiles from the set of tiles, by removing the background tiles, c. encoding each tile or each selected tile, via a pre-trained model, via a pre-trained convolutional neural network, to obtain a representation vector or tensor for each tile concerned, d. assigning a score, also called attention score, to each tile, e. generate a global representation vector or tensor by aggregating all the vectors or tensors of each concerned tile, taking into account the aforementioned scores, for instance through a weighted sum of said vectors or tensors of the tiles, where the weight is the corresponding score of the vector or tensor of said tile, f. determining the class to which the image or at least a part of the image belongs, from the global representation vector or tensor, using a decision model, using a pre-trained neural network, of the fully connected type;

wherein the biological class is the genomic signature or profile of the cancer, or a molecular class of cancer, selected from triple negative breast cancer or luminal breast cancer, or the class is selected from the cancer's Grade, from the gBRCA1/2 (germline) status, selected from sporadic or germinal cancer, or from the homologous recombination status of a cancer, wherein the biological class is the genomic tumor (or cancer) profile, the Homologous Recombination Deficient (HRD) profile, defined by the presence of a germline BRCA1/2 (gBRCA1/2) mutation or assessed by the Large-scale State Transitions (LST) genomic signature.

2. The computer-implemented method according to claim 1, further comprising the following step:

classifying the image or at least a part of the image, from the global representation vector or tensor, using a decision model, using a pre-trained neural network of the fully connected type.

3. The computer-implemented method according to claim 1, wherein the pre-trained model of step (c) is trained using a self-supervised algorithm using a momentum contrast method.

4. The computer-implemented method according to claim 1, wherein the biological class of the biological image of a cancer tissue obtained from a subject is identified.

5. The computer-implemented method according to claim 1, wherein the neural network is specifically pre-trained on a set of images or sub-images of a cancer tissue obtained from one or more subjects to classify slide representations between HRD and non-HRD to the individual tile representations.

6. The computer-implemented method according to claim 1, wherein the images of sub-images are of known class.

7. The computer-implemented method according to claim 1, wherein, when training at least one of the aforementioned models, at least one bias is corrected, the bias selected from a bias related to the technique for obtaining the slide represented by said image, the fixing technique, the impregnation technique, and a bias related to a molecular subtype or a molecular class of cancer.

8. The computer-implemented method according to claim 1, wherein the biological image is a whole slide image (WSI), or a portion thereof.

9. The computer-implemented method according to claim 1, wherein the image is a visual representation of a body part using a medical technology imaging such as radiology, magnetic resonance imaging, ultrasound, endoscopy, elastography, tactile imaging, thermography, medical photography, nuclear medicine functional imaging techniques as positron emission tomography (PET) and single-photon emission computed tomography (SPECT).

10. The computer-implemented method according to claim 1, wherein the image is an image obtained from a tissue of a subject, a whole slide image obtained from a tissue of a subject, an image of a (histo) pathology section, or a digitized image of (histo) pathology section.

11. The computer-implemented method according to claim 10, wherein the tissue is a cancer, or tumor, tissue.

12. The computer-implemented method according to claim 11, wherein the cancer or tumor is selected from cancers or tumors deficient in homologous recombination (HRD).

13. The computer-implemented method according to claim 11, wherein the cancer is selected from breast cancers, ovarian cancers, liver cancers, esophageal cancers, lung cancers, head and neck cancers, prostate cancers, colon, rectal, or colorectal cancers, and pancreatic cancers.

14. The computer-implemented method according to claim 11, wherein the cancer or tumor is a primary or a metastatic cancer or tumor.

15. The computer-implemented method according to claim 11, wherein the breast cancer is a luminal (luminal A or luminal B) breast cancer, a triple-negative/basal-like breast cancer (TNBC), an HER2-enriched breast, or a normal-like breast cancer.

16. The computer-implemented method according to claim 10, wherein the tissue is derived from a biopsy selected from a cancer or tumor biopsy.

17. The computer-implemented method according to claim 1, wherein the training set of images or sub-images is obtained from a set of biological images, from one or more subjects, of one type of cancer, of one molecular type of cancer.

18. A method according to claim 1, wherein the training set of images are stratified in sub groups according to various technical features, selected from the follow group: the type of image, the type of staining, the type of tissue fixation, and biological features.

19. The computer-implemented method according to claim 1, wherein sampling of the training set of images or of the set of tiles is performed before the training of the neural network.

20. The computer-implemented method according to claim 1, wherein subgroups of images are selected for specific training of the neural network, wherein the images are whole slide images from stained histopathological section of luminal and triple-negative breast cancers, wherein the histological sections are stained with Hematoxylin Eosin (HE).

21. A computer-implemented method for visualizing clusters of sub-images or tiles of at least one biological class, of at least one biological image, comprising the following steps:

a. dividing the image into sub-images or tiles, b. selecting at least some of the tiles from the set of tiles by removing the background tiles, c. encoding each tile or each selected tile, via a pre-trained convolutional neural network, so as to obtain a representation vector or tensor for each tile;

d. assigning a score, also called attention score, to each tile, e. selecting tiles based on the attention score by selecting the tiles with the highest attention scores, f. assigning a score, also called decision score, to each tile by predicting the output class from each individual tile, g. further selecting tiles, as to keep only tiles that have both a high attention and a high decision score, h. projecting the tile representation of said tiles or said selected tiles to a a 2-dimensional or 3-dimensional space by using the U-MAP (Uniform Manifold Approximation and Projection) or T-SNE (T-distributed Stochastic Neighbor Embedding) algorithm, wherein the biological class is the genomic signature or profile of the cancer, or a molecular class of cancer, selected from triple negative breast cancer or luminal breast cancer, or the class is selected from the cancer's Grade, from the gBRCA1/2 (germline) status, selected from sporadic or germinal cancer, or from the homologous recombination status of a cancer, wherein the biological class is the genomic tumor (or cancer) profile, a Homologous Recombination Deficient (HRD) profile, defined by the presence of a germline BRCA1/2 (gBRCA1/2) mutation or assessed by Large-scale State Transitions (LST) genomic signature.

22. The computer-implemented method according to claim 21, which further comprises the following steps:

i. identify clusters of tile representations in the low dimensional space, j. label at least part of said clusters and/or identify a feature, or a combination of features or pattern(s) in the tiles belonging to at least part of said clusters.

23. A computer-implemented method for identifying a phenotypical feature, or a combination of phenotypical features or phenotypical pattern in a biological image from a subject, wherein said image is examined for assessing the presence of said phenotypical feature or combination of phenotypical features or phenotypical pattern(s) as defined at step h) of claim 21, wherein the phenotypical feature is a histopathological feature.

* * * * *